US012648571B2

(12) United States Patent
Nicolau et al.

(10) Patent No.: US 12,648,571 B2
(45) Date of Patent: Jun. 9, 2026

(54) COMPOSITIONS INCLUDING ANTIMICROBIAL POLYMER-PEPTIDE CONJUGATES AND USES THEREOF

(71) Applicant: University of Puerto Rico, San Juan, PR (US)

(72) Inventors: Eduardo Nicolau, San Juan, PR (US); Valerie Ortiz Gómez, San Juan, PR (US)

(73) Assignee: University of Puerto Rico, San Juan, PR (US)

(*) Notice: Subject to any disclaimer, the term of this patent is extended or adjusted under 35 U.S.C. 154(b) by 802 days.

(21) Appl. No.: 17/795,129

(22) PCT Filed: Jan. 26, 2021

(86) PCT No.: PCT/US2021/015049
§ 371 (c)(1),
(2) Date: Jul. 25, 2022

(87) PCT Pub. No.: WO2021/154703
PCT Pub. Date: Aug. 5, 2021

(65) Prior Publication Data
US 2023/0072630 A1 Mar. 9, 2023

Related U.S. Application Data

(60) Provisional application No. 62/966,362, filed on Jan. 27, 2020.

(51) Int. Cl.
| | |
|---|---|
| *A01N 63/50* | (2020.01) |
| *A01N 25/10* | (2006.01) |
| *A01P 1/00* | (2006.01) |
| *A61K 47/54* | (2017.01) |
| *A61K 47/60* | (2017.01) |
| *A61L 29/04* | (2006.01) |
| *A61L 31/04* | (2006.01) |
| *A61P 31/04* | (2006.01) |

(52) U.S. Cl.
CPC ............. *A01N 63/50* (2020.01); *A01N 25/10* (2013.01); *A01P 1/00* (2021.08); *A61K 47/545* (2017.08); *A61K 47/60* (2017.08); *A61L 29/049* (2013.01); *A61L 31/041* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 2010/0316643 A1* | 12/2010 | Eckert ..................... | A61P 33/02 514/21.3 |
| 2014/0309161 A1 | 10/2014 | Hoffmann et al. | |

OTHER PUBLICATIONS

Hersh et al., Clinical Infectious Diseases 2012;54(11):1677-8 (Year: 2012).*
Aspergillosis, downloaded from URL:<http://patient.info/doctor/aspergillosis> (Year: 2016).*
International Search Report and Written Opinion on PCT PCT/US2021/015049 dated May 7, 2021 (9 pages).
Li et al., "Membrane Active Antimicrobial Peptides: Translating Mechanistic Insights to Design," Frontiers in Neuroscience, vol. 11, Article 73, Feb. 14, 2017 (18 pages) doi: 10.3389/fnins.2017.00073.

* cited by examiner

*Primary Examiner* — Sergio Coffa
(74) *Attorney, Agent, or Firm* — Foley & Lardner LLP

(57) ABSTRACT

Disclosed herein are PEG-maximin H5 peptide conjugates and methods for using the same in the treatment or prevention of biofilms and biofouling.

20 Claims, 21 Drawing Sheets

Specification includes a Sequence Listing.

MH5C-Cys                mPEG-Maleimide                MH5C-Cys
                                                      conjugated

FIG. 1

| Temperature (°C) | α-helix | β-sheet | Random coil |
|---|---|---|---|
| 20 | 95.29% | 0.02% | 4.69% |
| 30 | 95.35% | 0.02% | 4.63% |
| 40 | 95.50% | 0.02% | 4.48% |
| 50 | 95.46% | 0.01% | 4.53% |
| 60 | 95.39% | 0.01% | 4.60% |
| 70 | 95.01% | 0.01% | 4.99% |
| 80 | 94.78% | 0.01% | 5.21% |
| 90 | 94.13% | 0.01% | 5.86% |

| Temperature (°C) | α-helix | β-sheet | Random coil |
|---|---|---|---|
| 20 | 95.22% | 0.02% | 4.76% |
| 30 | 95.50% | 0.02% | 4.48% |
| 40 | 95.46% | 0.01% | 4.53% |
| 50 | 95.28% | 0.01% | 4.71% |
| 60 | 94.91% | 0.01% | 5.08% |
| 70 | 94.64% | 0.02% | 5.34% |
| 80 | 93.62% | 0.02% | 6.36% |
| 90 | 68.76% | 0.03% | 31.21% |

(A)

(B)

Control
(Bacteria and Nutrient Broth)

Experimentl
(Bacteria and AMP's)

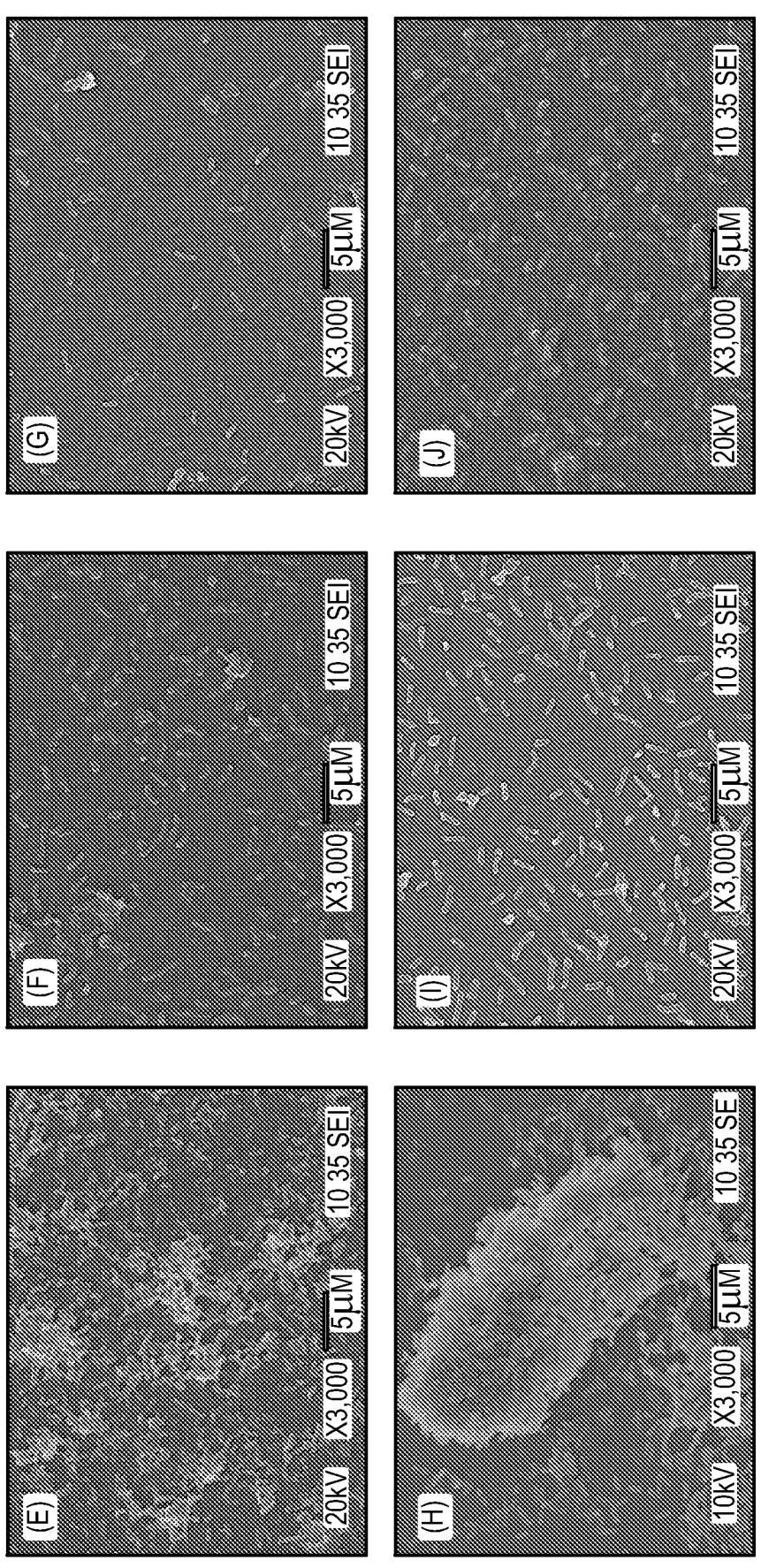
FIG. 10 (Contd.)

FIG. 11

*E. coli*

| antimicrobial assays | MH5C-Cys | MH5C-Cys-PEG 2 kDa | MH5C-Cys-PEG 5 kDa |
|---|---|---|---|
| MIC | 90 | 40 | 40 |
| MBIC | NAD | NAD | 300 |
| MBEC | NAD | NAD | 500 |

FIG. 20

COMPOSITIONS INCLUDING ANTIMICROBIAL POLYMER-PEPTIDE CONJUGATES AND USES THEREOF

CROSS-REFERENCE TO RELATED APPLICATIONS

This application is a U.S. National Stage Application under 35 U.S.C. § 371 of International Patent Application No. PCT/US2021/015049, filed on Jan. 26, 2021, which claims the benefit of and priority to U.S. Provisional Patent Application No. 62/966,362, filed Jan. 27, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 8, 2021, is named 118347-0106_SL.txt and is 1,479 bytes in size.

TECHNICAL FIELD

The present disclosure relates to compositions including PEG-maximin H5 peptide conjugates, and methods of using the same for preventing or inhibiting bacterial growth.

BACKGROUND

Many pathogens, such as *Pseudomonas aeruginosa* and *Escherichia coli* bacteria can easily attach to surfaces and form stable biofilms. The formation of microbial biofilms on surfaces represents a problem for many important applications such as membrane-based water purification, as well as biomedical and industrial processes. Biofilms are a major concern when introducing products into the human body (e.g., contact lenses, central venous catheters, mechanical heart valves and pacemakers). Biofilms also pose a problem in many industries including the food, pharmaceutical, paint, water, shipping and engineering industries causing, amongst a wide range of negative effects, accelerated corrosion in industrial systems, oil souring and biofouling. For example, biofouling may be caused by the adhesion of organisms to any surface in a marine or freshwater environment, including cooling towers, water pipes and filters in cooling or desalinization installations, irrigation and power stations, and membranes, such as those used in wastewater and desalinization systems. Biofouling also occurs in aquaculture systems in fish farms. Further, the commercial shipping fleets of the world consume approximately 300 million tons of fuel annually. Without antifouling measures, fuel consumption would increase by as much as 40% (equivalent to an extra 120 million tons of fuel annually), which is associated with an economic cost of about $7.5 billion in 2000 and $30 billion currently.

Biofilms are very difficult to eliminate since the constituent microbes are highly organized and can withstand hostile environments, such as high temperatures and antimicrobial agents (e.g., antibiotics).

SUMMARY OF THE PRESENT TECHNOLOGY

In one aspect, the present disclosure provides a peptide conjugate comprising a polyethylene glycol (PEG) polymer conjugated to an antimicrobial peptide (AMP) comprising the amino acid sequence ILGPVLGLVSDTLDDVLGIL- COOH (SEQ ID NO: 1) or ILGPVLGLVSDTLDDVLGILC-COOH (SEQ ID NO: 2). In another aspect, the present disclosure provides a peptide conjugate comprising a polyethylene glycol (PEG) polymer conjugated to an antimicrobial peptide (AMP) having an amino acid sequence of ILGPVLGLVSDTLDDVLGIL-COOH (SEQ ID NO: 1) or ILGPVLGLVSDTLDDVLGILC-COOH (SEQ ID NO: 2), or a variant thereof comprising one or more conservative substitutions. In some embodiments of the peptide conjugates disclosed herein, the PEG polymer is conjugated to the N-terminus or the C-terminus of the AMP or the variant thereof. The peptide conjugates of the present technology may further comprise a cysteine residue at the N-terminus or the C-terminus of the AMP.

Additionally or alternatively, in some embodiments of the peptide conjugates of the present technology, the AMP is between about 20 to about 30 amino acids in length or between about 20 to about 25 amino acids in length. In any and all embodiments of the peptide conjugates disclosed herein, the PEG polymer has an average molecular weight of about 1 kDa to about 50 kDa. In certain embodiments, the PEG polymer has an average molecular weight of 2 kDa or 5 kDa. Additionally or alternatively, in some embodiments, the PEG polymer comprises between about 40 to about 200 ethylene oxide units. In other embodiments, the PEG polymer comprises greater than about 40 ethylene oxide units or greater than about 100 ethylene oxide units.

Additionally or alternatively, in some embodiments of the peptide conjugates of the present technology, the AMP comprises a secondary structure that is at least about 90%-95% α-helix, and/or less than about 1%, less than about 0.5%, less than about 0.1%, or less than about 0.05% β-sheet.

In one aspect, the present disclosure provides a medical implant or device comprising a body having at least one surface, wherein the at least one surface is coated with, or includes an effective amount of any of the peptide conjugates disclosed herein. In some embodiments of the medical implant or device, the at least one surface is composed of a synthetic carbon polymer and/or a polypeptide. In some embodiments, the medical implant is a vascular graft. Examples of suitable medical devices include, but are not limited to, a fracture fixation system, a tubular device that penetrates a body tissue of a patient, and a component of an intubation system. In certain embodiments, the fracture fixation system is a nail, a bolt, or a screw. In some embodiments, the tubular structure is selected from the group consisting of an intubation tube, a feeding tube, an endotracheal tube, a catheter, and a shunt.

Additionally or alternatively, in some embodiments of the medical implants or devices disclosed herein, the at least one surface is coated with the peptide conjugate at a surface density ranging from 0.4 to 275 micrograms per square centimeter.

In one aspect, the present disclosure provides a method for preventing or treating an infection caused by a microbial pathogen in a subject in need thereof comprising administering to the subject any of the medical implants or devices disclosed herein. Also disclosed herein are methods for preventing or eradicating biofilm formation caused by a microbial pathogen in a subject in need thereof comprising administering to the subject any of the medical implants or devices described herein. Additionally or alternatively, in some embodiments of the methods disclosed herein, the subject suffers from or is at risk for endocarditis, urinary tract infections, biliary sepsis, pneumonia, gastroenteritis, cystic fibrosis, or burn wounds. In some embodiments of the methods disclosed herein, the microbial pathogen comprises a population of gram-negative or gram-positive bacteria. In some embodiments, the microbial pathogen is *P. aeruginosa* or *E. coli*.

In one aspect, the present disclosure provides a method for reducing microbial biofilm formation on a surface comprising contacting the surface with an effective amount of a composition comprising any of the peptide conjugates disclosed herein. The microbial biofilm formation may be caused by gram-positive or gram-negative bacteria. In another aspect, the present disclosure provides a method for inhibiting growth of a microbe population on a surface comprising contacting the surface with an effective amount of a composition comprising any of the peptide conjugates of the present technology. In certain embodiments, the microbe population comprises gram-positive or gram-negative bacteria. Examples of gram-negative bacteria include, but are not limited to, *P. aeruginosa* or *E. coli*.

In any and all of the above embodiments of the methods disclosed herein, the Minimal Inhibitory Concentration (MIC) or Minimum Biofilm Eradication Concentration (MBEC) of the peptide conjugate is between about 50 µM and about 500 µM.

In one aspect, the present disclosure provides a method for reducing aquatic biofouling in an aquatic environment comprising: contacting the aquatic environment with an effective amount of any of the peptide conjugate of the present technology. Also provided herein is an aquatic filtration membrane comprising any of the peptide conjugates disclosed herein.

In another aspect, the present disclosure provides a method for preventing or reducing biofilm formation in water comprising contacting the water with an effective amount of a composition comprising any of the peptide conjugates disclosed herein. Also disclosed herein are methods for preventing or reducing biofilm formation in a fluid medium comprising contacting the fluid medium with an effective amount of a composition comprising any of the peptide conjugates of the present technology. In some embodiments, the contacted water or fluid medium is applied to a reverse osmosis filter.

In yet another aspect, the present disclosure provides a method for fabricating a medical device or implant that is configured to eradicate or prevent biofilm formation comprising contacting at least one surface of a body of a medical device or implant with an effective amount of any of the peptide conjugates disclosed herein.

BRIEF DESCRIPTION OF THE DRAWINGS

FIG. 1 exemplifies a bioconjugation covalent reaction between MH5C-Cys and PEG via thiol-maleimide chemistry.

FIG. 5(A) and FIG. 5(C) growth curves of bacteria, FIG. 5(B) and FIG. 5(D) indicate statistical differences. The concentration of these bacteria is $1.0 \times 10^8$ CFU/mL. The statistically significant differences between control and AMPs are demonstrated in asterisks (P<0.0001; n=3 in each time point).

FIG. 7.1 illustrates inhibitory activity of the peptides on biofilm formation by *P. aeruginosa*. FIG. 7.1(A) control (bacteria and nutrient broth), FIG. 7.1(B) MH5C, and FIG. 7.1(C) MH5C-Cys. FIG. 7.2 illustrates inhibitory activity of the peptides on biofilm formation by *E. coli*. FIG. 7.2(A) control (bacteria and nutrient broth), FIG. 7.2(B) MH5C, and FIG. 7.2(C) MH5C-Cys.

FIG. 8(A) *E. coli* and FIG. 8(B) *Pseudomonas aeruginosa* are control samples (i.e., bacteria and nutrient broth). Biofilm formation was observed for *E. coli* with unconjugated PEG 2 kDa (FIG. 8(C)) and PEG 5 kDa (FIG. 8(D)) (i.e., bacteria, nutrient broth and PEG polymer without peptide). Biofilm formation was also observed for *P. aeruginosa* with unconjugated PEG 2 kDa (FIG. 8(E)) and PEG 5 kDa (FIG. 8(F)) (i.e., bacteria, nutrient broth and PEG polymer without peptide).

FIG. 9(A): Analytical Size Exclusion, at 220 nm. Presented in red the conjugate with PEG 5 kDa, in blue the conjugate with PEG 2 kDa and finally in black the MH5C-Cys. FIG. 9(B) SDS PAGE of peptide-polymer conjugate: Lane 1: Dual Xtra Standards (ladder), lane 2: IVII-I5C-Cys and lane 3: MH5C-Cys conjugated with PEG. FIG. 9(C) MALDI-ToF spectra: black and gray lines denote the PEG and the PEG-MH5C-Cys conjugate, respectively. These techniques were employed with the objective of characterizing and analyzing bioconjugation through molecular weight.

FIG. 10(A) and FIG. 10(C) represent growth curves of bacteria, FIG. 10(B) and FIG. 10(D) indicate statistical differences (P<0.0001; n=3 in each time point). FIG. 10(E) and FIG. 10(H) are untreated *P. aeruginosa* and *E. coli* controls for biofilm formation, respectively. FIG. 10(F) and FIG. 10(G) show inhibition of *P. aeruginosa* biofilms with MH5C-Cys-PEG 2 kDa and MH5C-Cys-PEG 5 kDa respectively. FIG. 10(I) and FIG. 10(J) show inhibition of *E. coli* biofilms with MH5C-Cys-PEG 2 kDa and MH5C-Cys-PEG 5 kDa respectively.

FIG. 11 illustrates Minimum Biofilm Inhibitory Concentration (MBIC) results using Colony Forming Units via spread plate method. The test plates contained serial dilutions of each conjugate and peptide (90 µM and 300 µM). Differences in CFU (Colony Forming Units), were taken as evidence of biofilm inhibition.

*aeruginosa*: FIG. 12(A) MH5C-Cys peptide, FIG. 12(B) MH5C-Cys-PEG 2 kDa and FIG. 12(C) MH5C-Cys-PEG 5 kDa. The initial concentration of bacteria is $1.0 \times 10^8$ CFU/mL. The samples were loaded at different concentrations (90, 300, and 500 μM).

FIG. 13(A) MH5C-Cys peptide, FIG. 13(B) MH5C-Cys-PEG 2 kDa and FIG. 13(C) MH5C-Cys-PEG 5 kDa. The initial concentration of bacteria is $1.0 \times 10^8$ CFU/mL. The samples were loaded at different concentrations (90, 300, and 500 μM).

FIG. 20 illustrates the summary of antimicrobial activity assay values in *P. aeruginosa* (ATCC 27853) and *E. coli* (ATCC 25922). All concentrations are reported as μM;

Figure 2:
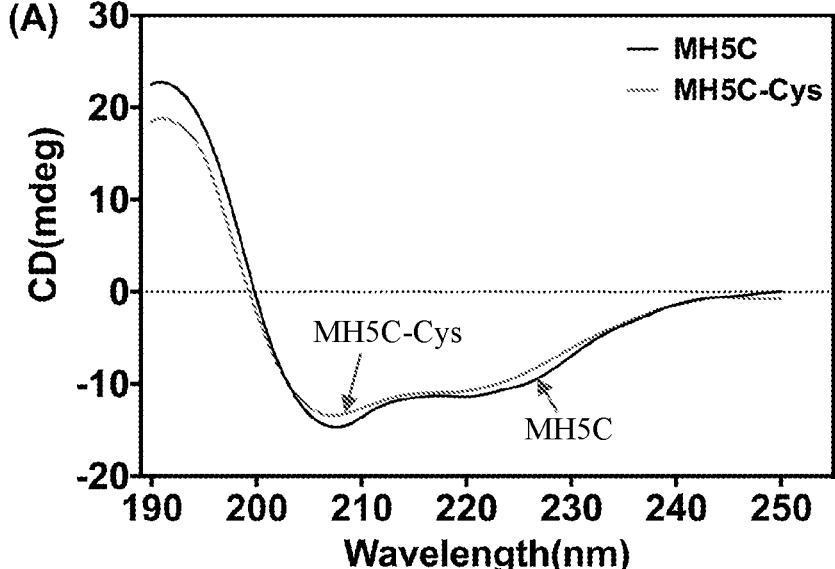
FIG. 2 illustrates CD structural analysis of MH5C, and MH5C-Cys peptides at 90 µM. Both possessed an α-helical structure and presented a stable folded process. Analysis of these spectra indicates the secondary structure is not altered by the modification at the C-terminus.

values were obtained from three to six independent experiments and were determined using a spectrophotometer (96-well plates) and Colony Forming Units (CFU/mL). These values are the same in both bacteria. NAD: no activity detected.

DETAILED DESCRIPTION

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) PCR 1: *A Practical Approach* (IRL Press at Oxford University Press); MacPherson et al. (1995) PCR 2: *A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Of all the pathogenic bacteria species present in nature, *P. aeruginosa* and *E. coli* represent two of the most deleterious. *E. coli*, a facultative anaerobic coliform bacterium, is implicated in urinary tract infections, biliary sepsis, pneumonia, gastroenteritis and many other illnesses. This bacteria is an indicator of fecal contamination in water and has been shown to clog water filters via biofouling. *P. aeruginosa* is an opportunistic waterborne pathogen with the ability of thriving in inhospitable environments. It is a frequent nosocomial infectious agent that can affect patients with cystic fibrosis, and burn wounds, leading to infections that can cause septicemia, meningitis and pneumonia. One of the reasons *P. aeruginosa* represents a challenge, similar to *E. coli*, is because of its ability to develop bacterial biofilms, or colonies of microorganisms that can grow on any surface. This microenvironment has become more tolerant to natural defenses and antibiotics making it a problem.

Some applications where protective coatings are beneficial include the membrane-based water purification field. In the water purification sector, one of the obstacles to the long-term efficiency of the membranes is biofilm formation that diminishes a filtration membrane's performance (Darling, S. B. *J. Appl. Phys.* 124 (3), 030901 (2018)). AMPs are biomolecules typically composed of 15-20 amino acids that are found in living organisms such as amphibians. As a survival mechanism, amphibians secrete AMPs that specifically target bacteria that frequent their environment, possibly including pathogens of interest. For example, the hydrophobic antimicrobial peptide maximin H5 (MH5) that can be abundantly found in the skin and brain of the Chinese frog *Bombina maxima* is an AMP with interesting features. This peptide is 20 amino acids in length (2 kDa) and contains three aspartate residues with no basic amino acid residues. The primary native structure of this anionic peptide is ILGPVLGLVSDTLDDVLGIL-NH2 (MHSN) (SEQ ID NO: 3).

Disclosed herein are Maximin H5 C-terminally deaminated isoforms (MH5C) modified with cysteine in the C-terminal (MH5C-Cys) and coupled to PEG polymers of different sizes (i.e., 2 kDa and 5 kDa) as well as their preventive antimicrobial potential. The polymer-peptide conjugates can be used as coatings to serve as protective barrier in surface applications.

The modified MH5C-Cys peptide retains the biophysical and antimicrobial characteristics of the Maximin H5 C-terminally deaminated isoform (MH5C). Disclosed herein is (1) the synthesis of PEG-MH5C-Cys conjugates that exhibited potent antimicrobial activity, and (2) the biophysical and antimicrobial characteristics of MH5C as an antimicrobial agent. Microbiological, physical and characterization analyses demonstrated that the MH5C-Cys peptide possesses significant antimicrobial effects and once coupled with PEG polymers maintained these essential characteristics.

Definitions

The definitions of certain terms as used in this specification are provided below. Unless defined otherwise, all technical and scientific terms used herein generally have the same meaning as commonly understood by one of ordinary skill in the art to which this present technology belongs.

As used herein and in the appended claims, singular articles such as "a", "an", and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

As used herein, the term "amino acid" includes naturally-occurring amino acids and synthetic amino acids, as well as amino acid analogs that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acids can be referred to herein by either their commonly known three letter symbols or by the one-letter symbols recommended by the IUPAC-IUB Biochemical Nomenclature Commission. Examples of "conservative substitutions" are provided below:

TABLE 1

| Amino Acid Substitutions | | |
| --- | --- | --- |
| Original Residue | Exemplary Substitutions | Conservative Substitutions |
| Ala (A) | val; leu; ile | val |
| Arg (R) | lys; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

"Hydrophobic amino acids" include, but are not limited to glycine, alanine, valine, leucine, isoleucine, phenylalanine, tryptophan, and methionine.

"Polar amino acids" include, but are not limited to, serine, threonine, cysteine, asparagine, glutamine and tyrosine.

As used herein, the term "biofilm" refers to an association of microorganisms, e.g., single or multiple species that can be encased or embedded in a matrix material, which may be self-produced by resident microorganisms. The biofilm may be present or adhere to living and/or non-living surfaces, e.g., tissue, a wound, medical implants, such as but not limited to orthopedic implants, dental implants, catheters, stents, etc. Exemplary microorganisms include, but are not limited to bacteria, e.g., Gram-negative bacteria, such as *Pseudomonas aeruginosa*, Gram-positive bacteria, such as *Staphylococcus aureus* and *Streptococcus mutans*, and fungi, such as yeasts, e.g., *Candida albicans*. The term "matrix material" is intended to encompass extracellular polymeric substances. Exemplary matrix materials include, but are not limited to polysaccharides, glycoproteins and/or nucleic acids. The term "biofilm" is further intended to include biological films that develop and persist at interfaces in aqueous environments. The language "biofilm development" or "biofilm formation" is intended to include the formation, growth, and modification of the bacterial colonies contained with biofilm structures, as well as the synthesis and maintenance of the exopolysaccharide of the biofilm structures. "Reducing" or "disrupting" a biofilm includes reducing the number of total viable microorganisms making up at least part of the biofilm, for example, as measured by total viable counts (TVC) of microorganisms (e.g., bacteria, yeast).

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking. The term "conjugating," and grammatical equivalents, when made in reference to conjugating a molecule of interest and a polymer means covalently linking the molecule of interest to the polymer. In some embodiments, the linkage may be direct. Alternatively, linkage may be indirect via a linking group or moiety. Methods for conjugation to polymers are known in the art, including methods for conjugation to a polypeptide to produce a fusion protein (Pasut, *Polymers* 6:160-178 (2014); Medscape, *Nanomedicine* 5(6):915-935 (2010)). In some embodiments, the conjugate comprises Maximin H5 conjugated to a PEG polymer. Precursors to such Maximin H5 conjugates, include a Maximin H5 peptide modified, e.g., with a linking group, but without the PEG polymer. The linking group links the polymer to the Maximin H5.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in eradicating or preventing biofilm formation. In the context of therapeutic and/or prophylactic applications, the agent (e.g., a polymer-peptide conjugate of the present technology) administered to the subject will vary depending on the composition, the degree, type, and severity of the condition (e.g., infection) and on the characteristics of the individual.

The term "Gram-positive bacteria" as used herein refers to bacteria characterized by having as part of their cell wall structure, peptidoglycan as well as polysaccharides and/or teichoic acids, and are characterized by their blue-violet color reaction in the Gram-staining procedure. Representative Gram-positive bacteria include: *Actinomyces* spp.,

*Bacillus anthracis, Bifidobacterium* spp., *Clostridium botulinum, Clostridium perfringens, Clostridium* spp., *Clostridium tetani, Corynebacterium diphtherias, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abscessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group *B streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *Streptococcus*), *Streptococcus salivarius, Streptococcus sanguis.*

The term "Gram-negative bacteria" as used herein refer to bacteria characterized by the presence of a double membrane surrounding each bacterial cell. Representative Gram-negative bacteria include *Acinetobacter calcoaceticus, Acinetobacter baumannii, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella pneumoniae, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prow azekii, Rickettsia rickettsii, Rochalimaea* spp., *Salmonella* spp., *Salmonella typhi, Serratia marcescens, Shigella* spp., *Shigella sonnei, Treponema carateum, Treponema pallidum, Treponema pallidum endemicum, Treponema pertenue, Veillonella* spp., *Vibrio cholerae, Vibrio vulnificus, Yersinia enterocolitica*, and *Yersinia pestis.*

As used herein, "polymer" is a substance that has a molecular structure containing chiefly or entirely a large number of similar units bonded together. Polymers may occur naturally (e.g., cellulose, polypeptides, nucleotides sequences, etc.) or are artificial (e.g., plastics, resins, etc.). Polymers may be used as carriers of drugs to which they are conjugated, and may enhance the solubility of the conjugated drug, improve pharmacokinetic profile of the drug, protect the drug against degradation, release the drug under certain conditions, such as change in pH or in the presence of enzymes, such as esterases, lipases or proteases. In addition, a targeting moiety or a solubilizer may also be introduced into the conjugate to boost its therapeutic index (Medscape, *Nanomedicine* 5(6):915-935(2010)). Polymers may also be utilized to restrict the distribution of the drug conjugated to it by, for example, preventing the conjugated drug from crossing into specific body compartments (e.g., from the gastrointestinal lumen to the underlying tissue). Polymers may be natural polymers and/or synthetic linear polymers, and include polyethylene glycol (PEG), dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly(hydroxyalkylmethaacrylamide), polyglycerol, polyamidoamine (PAMAM), polyethylenimine (PEI), and polypeptides.

As used herein, "prevention" or "preventing" of biofilm formation refers to a compound that, in a statistical sample, reduces the occurrence of biofilm formation in the treated sample relative to an untreated control sample, or delays the onset of one or more of biofilm formation relative to the untreated control sample.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, avian, etc. In some embodiments, the mammal is human.

"PEG" refers to polyethylene glycol, a linear polymer with terminal hydroxyl groups that has the formula HO—CH$_2$CH$_2$—(CH$_2$CH$_2$O)n-CH$_2$CH$_2$—OH, where n is from about 8 to about 4000. The terminal hydrogen may be substituted with a protective group such as an alkyl or alkanol group (M-PEG). In some embodiments, PEG has at least one hydroxy group, more preferably a terminal hydroxy group. In certain embodiments, the terminal hydroxy group is preferably activated to react with a peptide. There are many forms of PEG useful for the present technology and numerous derivatives of PEG exist in the art and are suitable for use in the present technology.

Peptide Conjugates of the Present Technology

Disclosed herein are antimicrobial peptide conjugates comprising C-terminally deaminated isoforms of Maximin H5 (MH5C; also SEQ ID NO: 1), an anionic hydrophobic AMP.

In one aspect, the present disclosure provides a peptide conjugate comprising a polyethylene glycol (PEG) polymer conjugated to an antimicrobial peptide (AMP) comprising the amino acid sequence ILGPVLGLVSDTLDDVLGIL-COOH (SEQ ID NO: 1) or ILGPVLGLVSDTLDDVLGILC-COOH (SEQ ID NO: 2). In another aspect, the present disclosure provides a peptide conjugate comprising a polyethylene glycol (PEG) polymer conjugated to an antimicrobial peptide (AMP) having an amino acid sequence of ILGPVLGLVSDTLDDVLGIL-COOH (SEQ ID NO: 1) or ILGPVLGLVSDTLDDVLGILC-COOH (SEQ ID NO: 2), or a variant thereof comprising one or more conservative substitutions. In some embodiments, the AMP further comprises a modification (e.g., at either terminus) that allows for covalent linkage of the PEG polymer to the AMP. For instance, the peptide conjugates of the present technology may further comprise a cysteine residue at the N-terminus or the C-terminus of the AMP.

Additionally or alternatively, in some embodiments of the peptide conjugates disclosed herein, the PEG polymer is conjugated to the N-terminus or the C-terminus of the AMP or the variant thereof. The PEG polymers may be functionalized with amine (NH$_2$) and/or aldehyde (CHO) that include linear mono-amines and mono-aldehydes, linear bi-amines and bi-aldehydes, multi-arm-amines and multi-arm-aldehydes, branched mono-, bi- and multi-armed-amines and aldehydes and multi-arm-forked-amines and aldehydes.

In some embodiments of the peptide conjugates disclosed herein, at least 10% of the amino acids of the AMP are acidic amino acids selected from Asp and Glu, or a combination thereof, and at least about 50% of the amino acids are hydrophobic amino acids. In some embodiments, about 5% to about 30% or about 10% to about 20%, or at least 15% of the amino acids of the AMP are acidic amino acids selected from Asp and Glu. In other embodiments, the AMP comprises about 10%, about 12%, about 14%, about 16%, about 18% or about 20% acidic amino acids, or a range between and including any two of the foregoing values. In some embodiments, the AMP comprises at least two Asp residues. In certain embodiments, the AMP comprises three Asp residues.

Additionally or alternatively, in some embodiments of the peptide conjugates disclosed herein, at least about 60%, at least about 70%, at least about 75%, or at least about 80% of the amino acids of the AMP are hydrophobic amino acids. In some embodiments, between about 70% to about 80% of the amino acids of the AMP are hydrophobic amino acids. In other embodiments, about 75% of the amino acids of the AMP are hydrophobic amino acids. Hydrophobic amino acids include, but are not limited to glycine, alanine, valine, leucine, isoleucine, phenylalanine, tryptophan, and methionine. In some embodiments of the peptide conjugates, the AMP comprises three or more leucine residues, e.g., 3, 4, 5, 6, 7, 8, 9 or 10 leucine residues. In certain embodiments, the AMP comprises 1, 2, 3, 4, or 5 isoleucine residues. In some embodiments, the AMP comprises 1, 2, 3, 4 or 5 phenylalanine residues. In some embodiments, the AMP comprises, 1, 2, 3, 4 or 5 glycine residues. In some embodiments, the AMP comprises 1, 2, 3, 4 or 5 valine residues.

Additionally or alternatively, in some embodiments of the peptide conjugates disclosed herein, about 0% to about 20% of the amino acids of the AMP are polar amino acids. In some embodiments, about 5% to about 20% of the amino acids of the AMP are polar amino acids. In other embodiments, about 10% of the amino acids are polar amino acids. In some embodiments, the polar amino acids of the AMP are selected from among serine and threonine.

Additionally or alternatively, in some embodiments of the peptide conjugates of the present technology, the AMP is between about 20 to about 50 amino acids in length. In some embodiments, the AMP is between about 20 to about 30 amino acids in length or between about 20 to about 25 amino acids in length. In certain embodiments, the AMP is about 20 amino acids in length. In other embodiments, the AMP is 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids in length, or a range between and including any two of the foregoing values.

In any and all embodiments of the peptide conjugates disclosed herein, the PEG polymer has an average molecular weight of about 1 kDa to about 50 kDa. In certain embodiments, the PEG polymer has an average molecular weight of 2 kDa or 5 kDa. Unless otherwise indicated, "average molecular weight" means weight average molecular weight. In some embodiments, the PEG polymer has an average molecular weight less than 10 kDa. In some embodiments, the average molecular weight of the PEG polymer is about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 20 kDa, 25 kDa, 30 kDa, 35 kDa, 40 kDa, 45 kDa, 50 kDa, or any range between and including two of these values.

Additionally or alternatively, in some embodiments, the PEG polymer comprises between about 40 to about 200 ethylene oxide units. In other embodiments, the PEG polymer comprises greater than about 40 ethylene oxide units or greater than about 100 ethylene oxide units. In some embodiments, the PEG polymer comprises between about 100 to about 150 ethylene oxide units or between about 100 to about 125 ethylene oxide units. In some embodiments, the PEG polymer comprises between about 110 to about 120 ethylene oxide units, i.e., 110, 111, 112, 113, 114, 115, 116, 117, 118, 119, and 120 ethylene oxide subunits or a range between and including any two of the foregoing values. In other embodiments, the PEG polymer comprises between about 40-50 ethylene oxide subunits, i.e., 40, 41, 42, 43, 44, 45, 46, 47, 48, 49, 50 ethylene oxide subunits or a range between and including any two of the foregoing values.

Additionally or alternatively, in some embodiments of the peptide conjugates of the present technology, the AMP comprises a secondary structure that is at least about 90%-95% α-helix, and/or less than about 1%, less than about 0.5%, less than about 0.1%, or less than about 0.05% β-sheet. In some embodiments of the peptide conjugates of the present technology, the AMP has a secondary structure that is about 0.02% β-strand structure.

Additionally or alternatively, in some embodiments of the peptide conjugates disclosed herein, the AMP has a tilted conformation that allows interaction of the α-helical AMP with the lipids in the bacterial membrane at an angle of 30° to 60°.

In some embodiments, PEG has at least one hydroxy group, more preferably a terminal hydroxy group that is activated to react with the peptide. A variety of chemical modifications are used to prepare an active PEG derivative with a functional group, such as active carbonate, active ester, aldehyde, tresylate, or using PEG-propionaldehyde suitable for coupling to a given target molecule. The activated PEG derivative is then covalently linked to a reactive group on the polypeptide drug. There are many forms of PEG useful for the present technology and numerous derivatives of PEG exist in the art and are suitable for use in the present technology. It is most preferable that there be one PEG molecule per AMP; however, when more than one PEG molecule per peptide molecule is present, it is preferred that there are no more than six. It is further contemplated that both ends of the PEG molecule may adapted for cross-linking two or more AMPS together. Methods of attaching PEG molecules to proteins, and fragments thereof, are well known in the art.

The PEG polymers described herein can have any of a number of different geometries. For example, in some embodiments, the polymers are linear polymers, branched polymers, forked polymers, or a combination of any of these polymers.

The antimicrobial peptide-polymer conjugates and precursors may be prepared using standard techniques known in the art. In some embodiments, a difunctional linker containing at least two functional groups containing heteroatoms selected from N, O, and S in which one of the functional groups is protected, may be conjugated using standard ester, thioester and amide bond forming technology. For example, a diamino-alkylene linker in which one of the amino groups is protected by a urethane protecting group (e.g., Boc. Cbz, etc.) may be coupled to cyclosporine A in the presence of a coupling agent (e.g., DCC, EDC/HOBt, etc.). Alternatively, an active ester, mixed anhydride or acid halide derivative of cyclosporine A may be prepared and reacted with the mono-protected diamine. (See, for example, Bodansky, M. & Bodanszky, A., The Practice of Peptide Synthesis, Springer-Verlag, New York, 1984.) The protecting group may be removed and the free amine reacted with an alde-hyde derivative of the polymer under reducing conditions to provide the conjugate. Similarly, a linker with a protected aldehyde (e.g., 1,1-dimethoxy) and an amine may be coupled to the cyclosporine A, deprotected to form the aldehyde and subjected to reductive amination with an amino-bearing polymer to form the conjugate. Variations of these schemes using α,ω-carboxy amines, α,ω-aminoalco-hols, α,ω-carboxyalcohols, α,ω-aminothiols, and the like to link cyclosporine A and the polymer will be readily under-stood by those of skill in the art.

Exemplary bacterial cells, whose adhesion may be pre-vented by the peptide conjugates disclosed herein include gram-positive bacteria and gram-negative bacteria. In some embodiments, the adhesion of gram-negative bacteria is prevented by a peptide conjugate disclosed herein. In some embodiments, the gram-negative bacteria is selected from among *Acinetobacter calcoaceticus, Acinetobacter bauman-nii, Actinobacillus actinomycetemcomitans, Aeromonas hydrophila, Alcaligenes xylosoxidans, Bacteroides, Bacte-roides fragilis, Bartonella bacilliformis, Bordetella* spp., *Borrelia burgdorferi, Branhamella catarrhalis, Brucella* spp., *Campylobacter* spp., *Chalmydia pneumoniae, Chla-mydia psittaci, Chlamydia trachomatis, Chromobacterium violaceum, Citrobacter* spp., *Eikenella corrodens, Entero-bacter aerogenes, Escherichia coli, Flavobacterium menin-gosepticum, Fusobacterium* spp., *Haemophilus influenzae, Haemophilus* spp., *Helicobacter pylori, Klebsiella pneumo-niae, Klebsiella* spp., *Legionella* spp., *Leptospira* spp., *Moraxella catarrhalis, Morganella morganii, Mycoplasma pneumoniae, Neisseria gonorrhoeae, Neisseria meningiti-dis, Pasteurella multocida, Plesiomonas shigelloides, Pre-votella* spp., *Proteus* spp., *Providencia rettgeri, Pseudomo-nas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Shi-gella sonnei, Treponema carateum, Treponema pallidum, Treponema pallidum endemicum, Treponema pertenue, Veil-lonella* spp., *Vibrio cholerae, Vibrio vulnificus, Yersinia enterocolitica,* and *Yersinia pestis.* In some embodiments, the gram-negative bacteria is selected from *P. aeruginosa* and *E. coli.*

In some embodiments, the gram-positive bacteria is selected from among *Actinomyces* spp., *Bacillus anthracis, Bifidobacterium* spp., *Clostridium botulinum, Clostridium perfringens, Clostridium* spp., *Clostridium tetani, Coryne-bacterium diphtheriae, Corynebacterium jeikeium, Entero-coccus faecalis, Enterococcus faecium, Erysipelothrix rhu-siopathiae, Eubacterium* spp., *Gardnerella vaginalis, Gemella morbillorum, Leuconostoc* spp., *Mycobacterium abscessus, Mycobacterium avium complex, Mycobacterium chelonae, Mycobacterium fortuitum, Mycobacterium hae-mophilium, Mycobacterium kansasii, Mycobacterium lep-rae, Mycobacterium marinum, Mycobacterium scrofula-ceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis,*

*Staphylococcus lugdanensis, Staphylococcus saccharolyti-cus, Staphylococcus saprophyticus, Staphylococcus schleif-eri, Staphylococcus similans, Staphylococcus warneri, Staphylococcus xylosus, Streptococcus agalactiae* (group B streptococcus), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *Streptococcus*), *Streptococcus salivarius,* and *Streptococcus sanguis.*

Medical Devices and Implants

In one aspect, the present disclosure provides a medical implant or device comprising a body having at least one surface, wherein the at least one surface is coated with, or includes an effective amount of any of the peptide conjugates disclosed herein. In some embodiments of the medical implant or device, the at least one surface is composed of a synthetic carbon polymer and/or a polypeptide. The medical implant or device may be extracorporeal or intracorporeal.

In some embodiments, the medical implant is a vascular graft. Examples of suitable medical devices include, but are not limited to, a fracture fixation system, a tubular device that penetrates a body tissue of a patient, and a component of an intubation system. In certain embodiments, the fracture fixation system is a nail, a bolt, or a screw. In some embodiments, the tubular structure is selected from the group consisting of an intubation tube, a feeding tube, an endotracheal tube, a catheter, and a shunt.

Additionally or alternatively, in some embodiments of the medical implants or devices disclosed herein, the at least one surface is coated with the peptide conjugate at a surface density ranging from 0.4 to 275 micrograms per square centimeter.

In yet another aspect, the present disclosure provides a method for fabricating a medical device or implant that is configured to eradicate or prevent biofilm formation comprising contacting at least one surface of a body of a medical device or implant with an effective amount of any of the peptide conjugates disclosed herein. The biofilm formation may be caused by a microbial pathogen. In some embodiments, the microbial pathogen is gram-negative or gram-positive bacteria.

Methods of Use

In one aspect, the present disclosure provides a method for preventing or treating an infection caused by a microbial pathogen in a subject in need thereof comprising administering to the subject any of the medical implants or devices disclosed herein. Also disclosed herein are methods for preventing or eradicating biofilm formation caused by a microbial pathogen in a subject in need thereof comprising administering to the subject any of the medical implants or devices described herein. Additionally or alternatively, in some embodiments of the methods disclosed herein, the subject suffers from or is at risk for endocarditis, urinary tract infections, biliary sepsis, pneumonia, gastroenteritis, cystic fibrosis, or burn wounds. In some embodiments of the methods disclosed herein, the microbial pathogen comprises a population of gram-negative or gram-positive bacteria. In some embodiments, the microbial pathogen is *P. aeruginosa* or *E. coli.*

In one aspect, the present disclosure provides a method for reducing microbial biofilm formation on a surface comprising contacting the surface with an effective amount of a composition comprising any of the peptide conjugates disclosed herein. The microbial biofilm formation may be caused by gram-positive or gram-negative bacteria. In another aspect, the present disclosure provides a method for inhibiting growth of a microbe population on a surface comprising contacting the surface with an effective amount of a composition comprising any of the peptide conjugates of the present technology. In certain embodiments, the microbe population comprises gram-positive or gram-negative bacteria. Examples of gram-negative bacteria include, but are not limited to, *P. aeruginosa* or *E. coli.*

In any and all of the above embodiments of the methods disclosed herein, the Minimal Inhibitory Concentration (MIC) or Minimum Biofilm Eradication Concentration (MBEC) of the peptide conjugates disclosed herein is between about 25 μM and about 500 μM or between about 50 μM and about 500 μM. In some embodiments, the MIC or MBEC of the peptide conjugates is between about 25 μM and about 250 μM between about 25 μM and about 200 μM between about 25 μM and about 150 μM between about 50 μM and about 150 μM or between about 75 μM and about 125 μM. In some embodiments, the MIC of a peptide conjugate described herein is about 100 μM or about 90 μM.

In one aspect, the present disclosure provides a method for reducing aquatic biofouling in an aquatic environment comprising: contacting the aquatic environment with an effective amount of any of the peptide conjugate of the present technology.

Also provided herein is an aquatic filtration membrane comprising any of the peptide conjugates disclosed herein.

In another aspect, the present disclosure provides a method for preventing or reducing biofilm formation in water comprising contacting the water with an effective amount of a composition comprising any of the peptide conjugates disclosed herein. Also disclosed herein are methods for preventing or reducing biofilm formation in a fluid medium comprising contacting the fluid medium with an effective amount of a composition comprising any of the peptide conjugates of the present technology. In some embodiments, the contacted water or fluid medium is applied to a reverse osmosis filter.

In any and all of the above embodiments of the methods disclosed herein, the Minimal Inhibitory Concentration (MIC) or Minimum Biofilm Eradication Concentration (MBEC) of the peptide conjugates disclosed herein is between about 25 μM and about 500 μM or between about 50 μM and about 500 μM. In some embodiments, the MIC or MBEC of the peptide conjugates is between about 25 μM and about 250 μM, between about 25 μM and about 200 μM, between about 25 μM and about 150 μM, between about 50 μM and about 150 μM, or between about 75 μM and about 125 μM. In some embodiments, the MIC of a peptide conjugate described herein is about 100 μM or about 90 μM.

EXAMPLES

The present technology is further illustrated by the following Examples, which should not be construed as limiting in any way.

Example 1—Physical Characterization of AMPs

Figure 1:
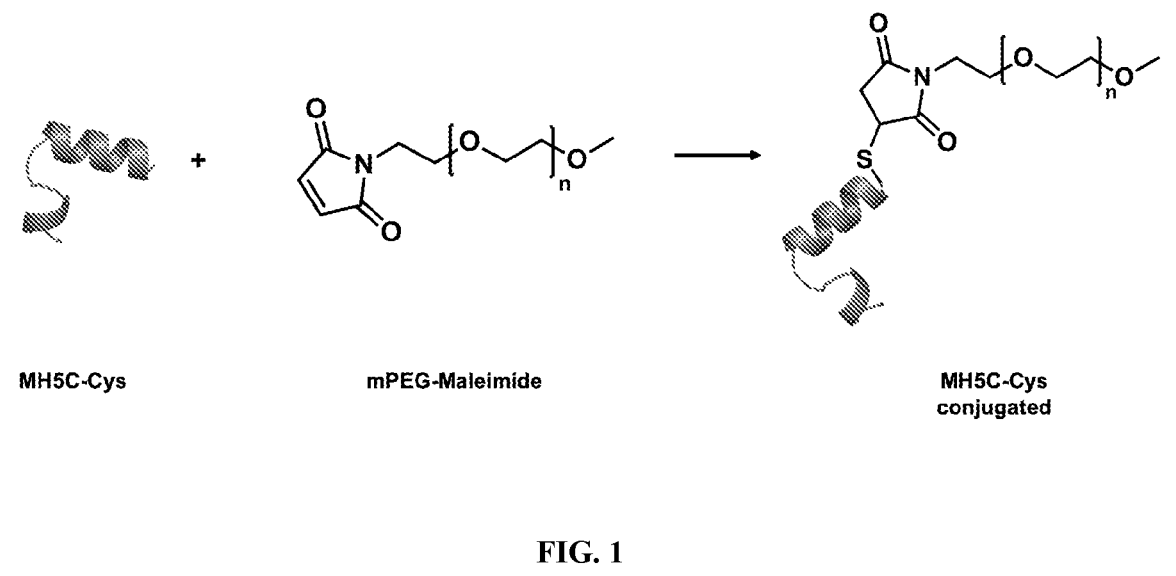

The antimicrobial peptide MH5C is a hydrophobic anionic molecule with 20 amino acids. In order to conjugate this peptide to the polymer, a modification to the C-terminal was introduced in the form of a cysteine. The modification with a cysteine allows the bioconjugation by having a maleimide modified polyethylene glycol (PEG). The imide selectively reacts to sulfhydryl functional groups on cysteine residues (FIG. 1).

The AMPs were purchased from GenScript Co. Maximin H5 C-terminally deaminated isoform (MH5C) (ILGPVLGLVSDTLDDVLGIL-COOH (SEQ ID NO: 1), 2,022.39 Da, 95% purity), Maximin H5 with cysteine (MH5C-Cys) ILGPVLGLVSDTLDDVLGILC-COOH (SEQ ID NO: 2), 2125.54 Da, 95% purity). Dimethyl Sulfoxide (DMSO, molecular biology 99% purity), Tris (2-carboxyethyl) phosphine hydrochloride (TCEP), Dulbecco's Phosphate Buffered Saline (DPBS) was purchased in Sigma Aldrich and used without further purification.

Before the peptide was coupled to the polymer, the effects of the modification to the peptide's C-terminal were studied. As such, physical and biological characterization tests if the MH5C and MH5C-Cys peptide were conducted.

Dynamic Light Scattering (DLS)

To determine the stability of the peptide in solution, DLS was conducted for both peptides (MH5C and MH5C-Cys).

AMPs were dissolved in DMSO and nanopure water (DMSO/np water mixture; 20% v/v) with the final concentration at 1.0 mg/mL. First the samples were ultra-centrifuged (29,100 rpm, 1 hour at 20° C.) and later the size average of these biomolecules was studied in solution using a Malvern Zetasizer Nano instrument (4 mW 632.8 nm laser). The individual peak method was used to determine the Polydispersity Index (PdI).

The average apparent hydrodynamic diameter results showed that the MH5C peptide has a hydrodynamic diameter of 0.72±0.11 d. nm (PDI=0.03), whereas MH5C-Cys, displayed a small decrease resulting in 0.52±0.44 d. nm (PDI=0.01).[35] These results suggest that these peptides do not tend to aggregate and are stable in the experimental conditions and after the cysteine modification.[25]

Likewise, zeta potential was conducted in order to determine the overall charge of the modified and unmodified peptide. The zeta potential is highly dependent on the pH as it directly affects the overall charge of the colloidal species. Therefore, it was of interest to know the isoelectric point of the peptides. Using ExPASy ProtParam tool (https://web-.expasy.org/protparam/), the theoretical isoelectric points of MH5C and MH5C-Cys, were determined at 3.42 in both cases. In this study the pH of each sample, MH5C was 4.5 and 5.9 for the MH5C-Cys. This is an important condition for the stability of the formulation, as no precipitation will occur under the conditions of the experiment.[36] MH5C had positive zeta potential values (46.6±0.9) compared to the MH5C-Cys (−94±4). In any case, a formulation with zeta potential values above and below ±30 is considered to be in a stable form.[37] Therefore, adding the cysteine to the peptide for further bioconjugation does not affect the peptide's stability per zeta potential measurements.

Circular Dichroism (CD) Spectroscopy

Another method to certify that the peptide's cysteine modification does not lead to significant structural changes is verification of the peptide's secondary structure via CD. The secondary structure is fundamental to the stability and efficiency of AMPS in terms of their biological activity.[38] Thus, changes in secondary structures may imply a decrease in the stability and antimicrobial function of the peptides.

Circular Dichroism spectra were recorded on a Jasco J-1500 CD Spectrometer (Jasco, Inc., Easton, MD). Both peptides (MH5C, MH5C-Cys) were dissolved according to the protocol published by Dennison et al. (2015) with 2,2,2-Trifluoroethanol and np water (TFE/np water mixture; 50% v/v) as co-solvent for this peptide.[26] The final concentration was set to 90 μM and the samples were ultra-centrifuged (29,100 rpm) for 1 hour at 20° C. Subsequently, 400 μL of the supernatant of each peptide was added to a rectangular quartz cell with 1 mm path length to evaluate secondary structures. The wavelength ranged from 250-190 nm and scanning speed was 50 nm/min at 20° C. The data obtained were triplicated and then averaged for each sample. In addition, the thermodynamics and unfolding of peptides was studied with this equipment. This technique was used to observe the secondary structure at wavelength complete spectra as a function of temperature.[27] The temperature range from 20° C. to 90° C. was used.

Analysis of the CD spectra showed MH5C had a 95.22% α helix structure and 0.02% β strand structure, whereas the MH5C-Cys resulted in 95.36% α helix structure and 0.02% β strand structure (FIG. 2). Spectra in these peptides presented negative bands in 208 nm and 220 nm, which is consistent to previous findings.[39]

For the secondary structure estimation, the K2D3 method was utilized as described elsewhere.[40] After obtaining the data, a predictive method that utilizes the information from the database Protein Data Bank (PDB) was employed. With this information, a theoretical prediction of CD, known as DichroCalc was obtained.[41] Then, the method K2D3 was utilized, which can predict secondary structures of peptides and proteins in recorded wavelengths between 200 nm to 240 nm in a non-redundant form. The results of these calculations are the predicted percentages for alpha-helix and beta-strand content.[40] The following equation was employed for this prediction:[42]

$$[\theta] = \frac{100(\text{signal})}{C \cdot n \cdot l}$$

where, $\lfloor \theta \rfloor$ is the mean residue ellipticity; C is the peptide concentration; n is the number of amino acid residues and l is the cell path length in cm.

Figure 3:
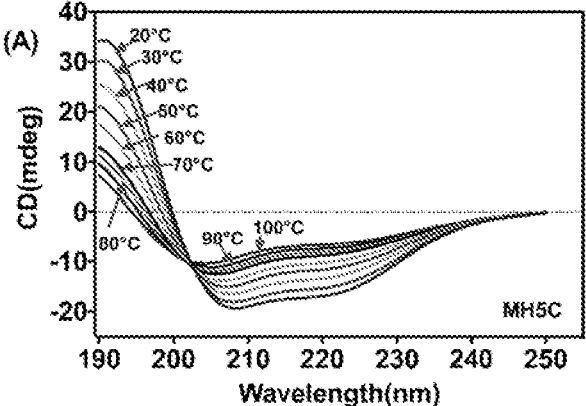
FIG. 3 illustrates CD spectra and percentages of secondary structure of MH5C antimicrobial peptides (AMPs) as a function of temperature. According to these results, the secondary structure represents stability throughout temperature increases.
Figure 3:
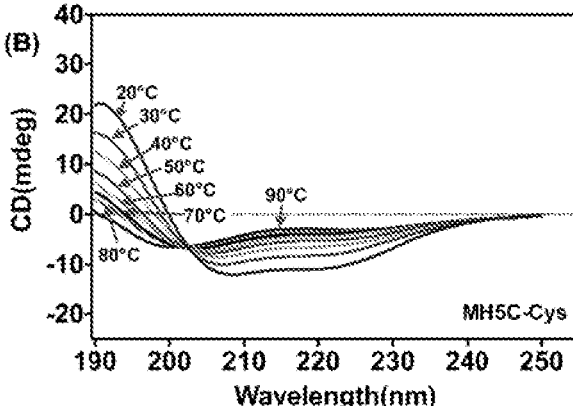

Analysis of these CD spectra showed that MH5 peptides possessed α-helical structure and were predominantly formed from random coil and minimum β-sheet structure, which corresponds with previous reports in literature.[26] The antimicrobial peptides with predominant α-helical structure demonstrate a robust antimicrobial activity and broad antimicrobial properties in Gram-negative and Gram-positive bacteria.[38] The secondary structure analysis was also performed with temperature variations from 20° C. to 90° C. in order to assess the thermal stability (FIG. 3).

Example 2—Microbiological Assays

To determine the antimicrobial activity of the peptides against the pathogenic bacteria P. aeruginosa (ATCC 27853) 22 and E. coli (ATCC 25922)23, the following materials were used: Costar 96-well plates Flat Bottom (Sterile Low Evaporation Lid, Corning, USA.), Calgary Biofilm Device (Innovotech Inc.), Glycerol 100% purity. The nutrient agar and broth used were BBL TSA II Trypticase Soy Agar (TSA) and BBL Trypticase Soy Broth (TSB) and were purchased from Becton, Dickinson and Company (BD).

For these assays, bacteria of interest were thawed, and serial cultured to reach optimal metabolic activity after being defrosted. Optical Density (O.D.) measured with a Genesys 10S UV-VIS Spectrophotometer (O.D.600 nm) was utilized as a measure of bacterial concentration, $1.0 \times 10^8$ CFU/mL, as standardized and approved by the Clinical and Laboratory Standards Institute (CLSI).[28] The final concentration of the solvent (vehicle control) was DMSO 10%.

Statistical Analysis

Statistical analyses were performed using the GraphPad Prism 6 software. All data were expressed as means ±standard errors of the means (SEM) and comparison of the means for the treatments was made at the 5% significance level. The data were analyzed with Two-way ANOVA with Dunnett's Test for multiple comparisons and were indicated the statistically differences with **** or p<0.0001.

Bacterial Growth Inhibition Test

To create growth curves of the bacteria with and without peptides and to determine the lowest concentration in which these antimicrobial peptides present inhibition of bacterial growth, Minimum Inhibition Concentration (MIC) testing was carried out. After thawing and incubating at 37° C. for 24 hours, and after achieving target O.D., the bacteria were placed on the 96-well plate with lid together with the peptides in various concentrations. Finally, the 96-well plate was taken to the Synergy H1TM Hybrid Multi-Mode Microplate Reader to observe and study the antibacterial effect of the peptides at 37° C. during different time points (0.5 h, 5 h, 12 h, 18 h and 24 h). This process that was used in the same in the evaluation of growth using the MH5C-Cys.

Figure 4:
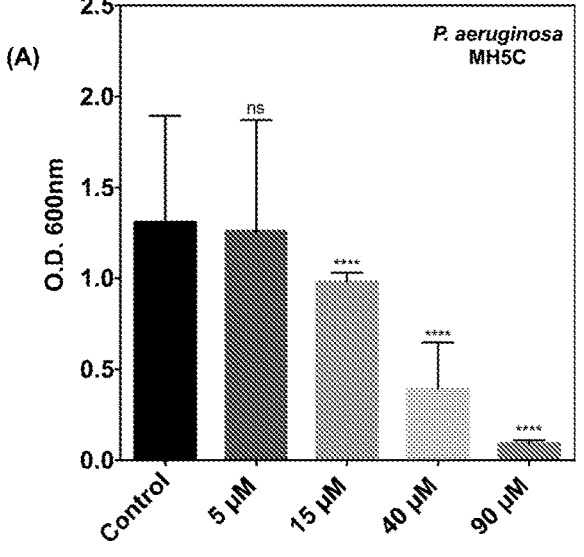
FIGS. 4(A)-4(B) illustrate the determination of the Minimum Inhibition Concentration in MH5C AMPs (FIG. 4(A) MH5C and FIG. 4(B) MH5C-Cys) after 24 hours of bacterial growth. Control (bacteria at a concentration of $1.0 \times 10^8$ CFU/mL and nutrient broth). *, , *, or **** indicate statistically differences with p<0.05, 0.005<p<0.05, 0.001<p<0.05, and p<0.001, respectively (n=3 in each time point).
Figure 4:
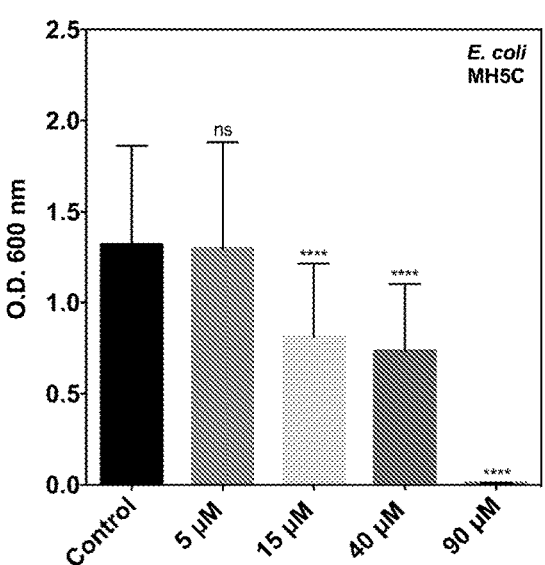
Figure 4:
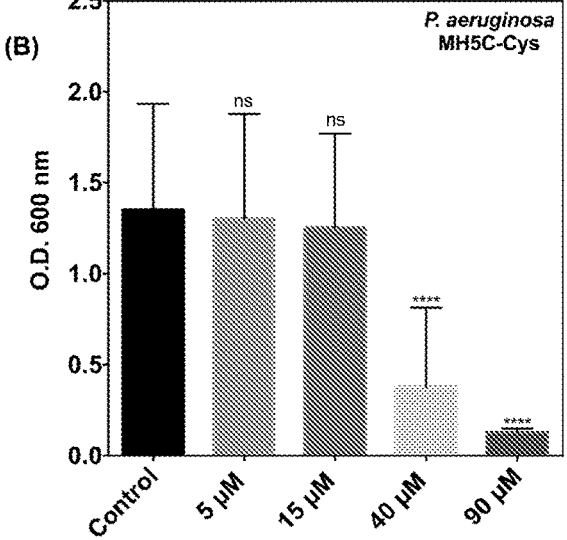
Figure 4:
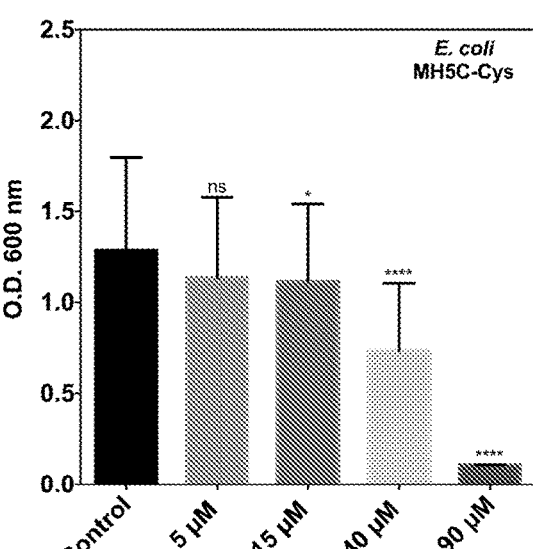
Figure 5:
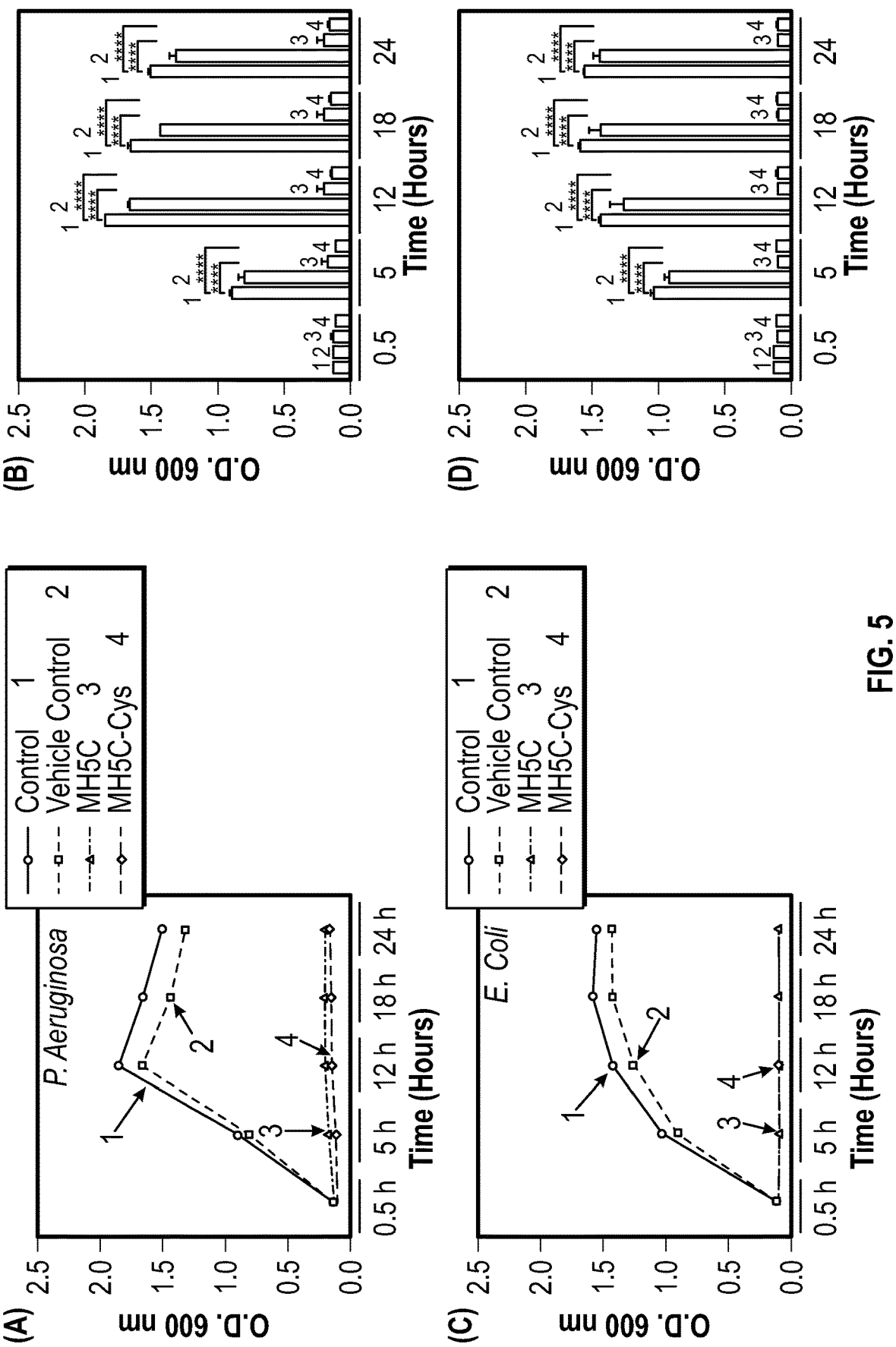
FIGS. 5(A)-5(D) illustrate bacterial inhibition tests using MH5C and MH5C-Cys peptides, control (bacteria and nutrient broth), and vehicle control (DMSO 10%).

Once it was determined that the MIC of these peptides was 90 μM (FIGS. 4A-4B), growth curves of both bacteria using the peptides were completed.[43] FIG. 5A and FIG. 5C shows the growth curves of bacteria with the antimicrobial peptides. It was determined that at 24 hours, the MH5C and MH5C-Cys did not allow bacterial growth. Further, the peptides demonstrate bacteriostatic effect in both bacteria after 12 hours of growth.[44] In MH5C and MH5C-Cys peptides, the solvent (vehicle control) does not have significant effect in the behavior of the bacteria strains. These results are demonstrated in FIG. 5B and FIG. 5D with statistically significant differences and p-value (p<0.0001).

The antibacterial activity of MH5C peptides is comparable with that of other anionic AMPs such as GH-11 L and GH-11 D from the frog Bombina orientalis.[45] These results confirm that the peptides MH5C and MH5C-Cys exhibit activity against these microorganisms, likely when in the planktonic phase. The bacteriostatic antimicrobial activity in this peptide is due to hydrophobic residues and α-helical structure. The most accepted mechanism of action for Maximin H5 peptide is the carpet model. Interestingly, the high content of hydrophobic residues in this peptide provides for a tilted conformation that allows interaction of the α-helical AMP with the lipids in the membrane in an angle of 30° to 60° that contributes to their ability to penetrate membranes. It is worth indicating that the net negative charge of MI-15C results from an internal cluster of D residues (aspartic acid) and appears to play no direct role in the membrane interactions.[17, 46] The antimicrobial activity of these peptides was tested in this study and exhibited activity against Gram-negative bacteria P. aeruginosa and E. coli, which is consistent with previous reports[17]

Scanning Electron Microscopy (SEM)—Study of Prevention in Biofilm Formation

Another important characterization was the determination of the feasibility of both the modified and unmodified peptide being able to prevent the formation of a biofilm. This was executed by taking images via SEM.

Figure 6:
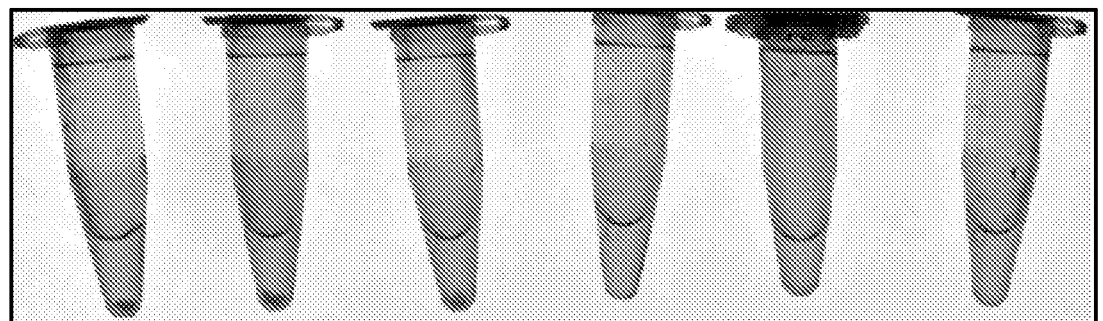
FIG. 6 illustrates bacterial pellet formation after 2 hours during SEM procedure. This pellet is formed before placing samples in a 24 well plate. Treatment with these biomolecules was effective in preventing biofilm formation.

For the examination, a JEOL 6480LV under high vacuum mode operating in a range of 10-20 kV. In brief, 100 μL of 1.0×10[8] CFU/mL cultures were grown in tubes at 37° C. with continuous shaking for 2 hours (direct contact between bacteria and antimicrobial peptides, (FIG. 6). The control group was bacteria with nutrient broth while the experimental group included bacteria with antimicrobial peptides (90

μM). After this procedure, samples were placed on a glass coverslip that was previously coated with poly-1-lysine (0.1% w/v Sigma Aldrich) to aid adhesion. Subsequently, the samples were placed in 24-well plates and incubated for 72 hours at 37° C. Sample fixation and dehydration were performed according to Bello et. al[29] as well as HMDS drying protocol as published elsewhere. 30 Finally, the samples were mounted on aluminum mount holders (12.2 mm) and sputtered with a thin gold film (ca. 5 nm thick). This process was also used in the evaluation of biofilm prevention using the MH5C-Cys.

Figure 7:
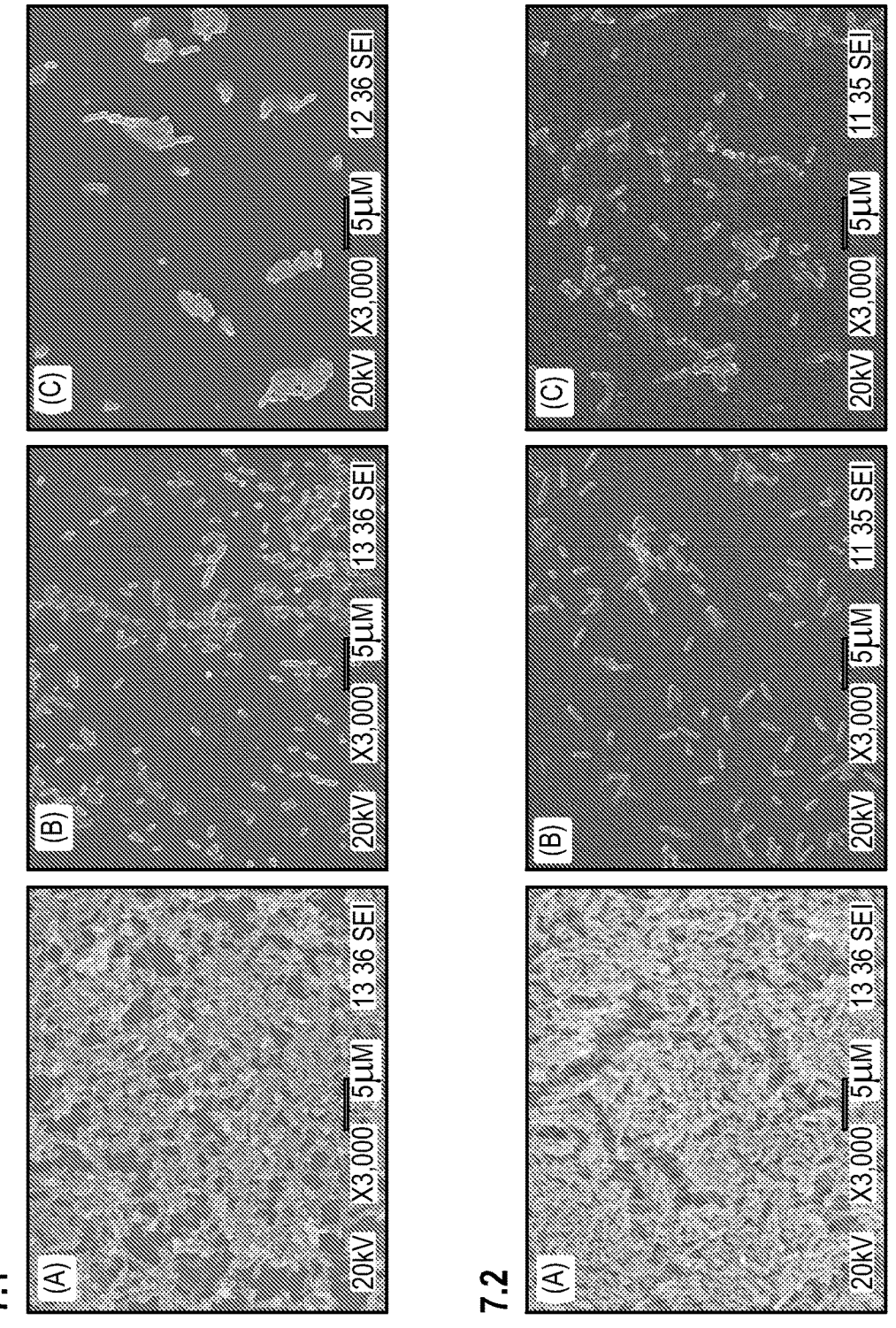
FIGS. 7.1-7.2 illustrate biofilm inhibition by MH5C and MHTC-Cys peptides.
Figure 8:
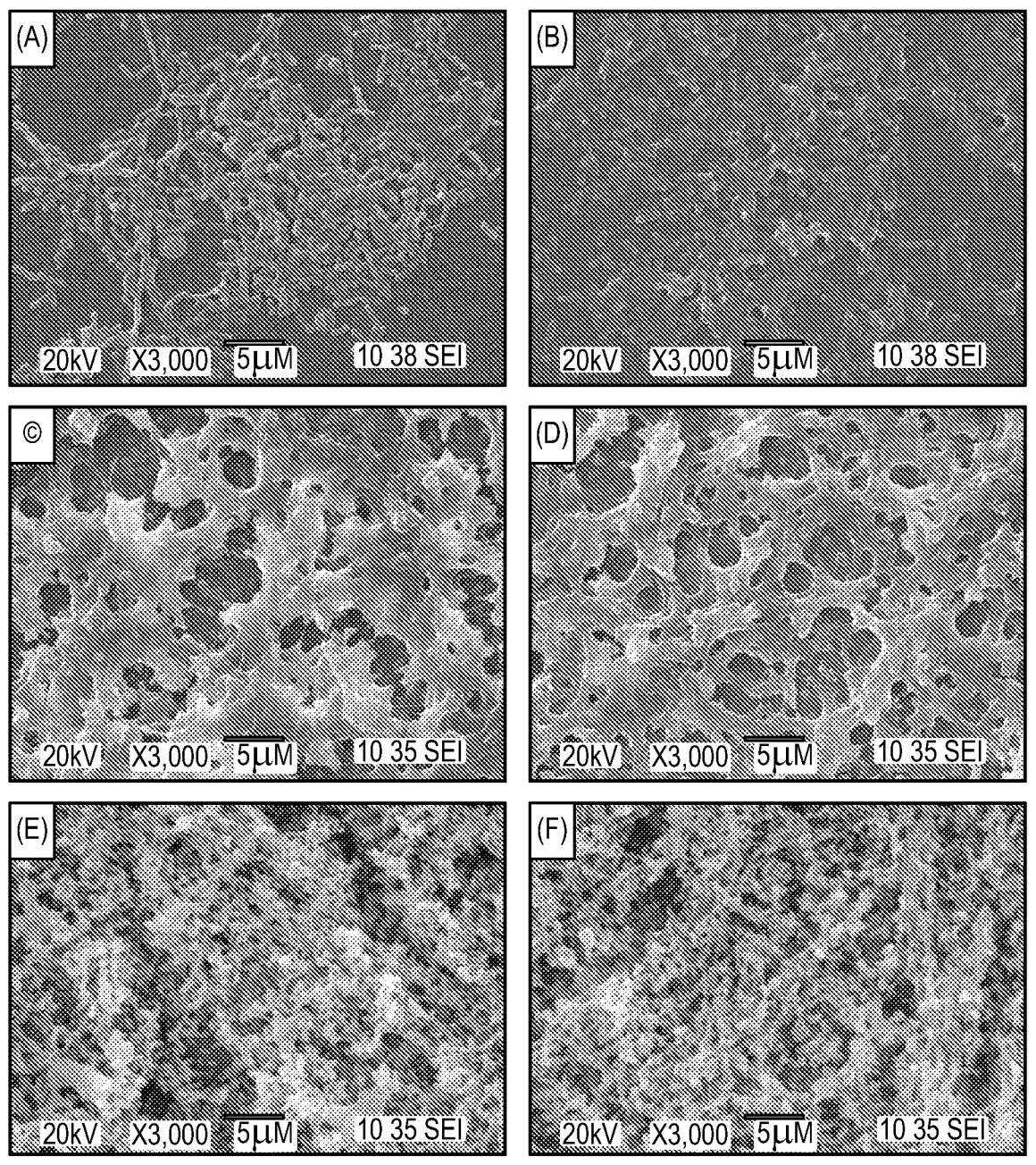
FIGS. 8(A)-8(F) illustrate biofilm formation observed with control samples.

As can be appreciated from FIG. 7, the antimicrobial peptides exhibited a significant prevention of the biofilm formation for P. aeruginosa and E. coli. These results validate the hypothesis that after direct contact of bacteria (e.g., in planktonic phase), these AMPS do not allow the production of a signaling pathway for cell communication between these bacteria (quorum sensing). The effect of preventing biofilm formation is solely ascribed to the peptides since PEG controls did not show any effect (FIG. 8).

Figure 14:
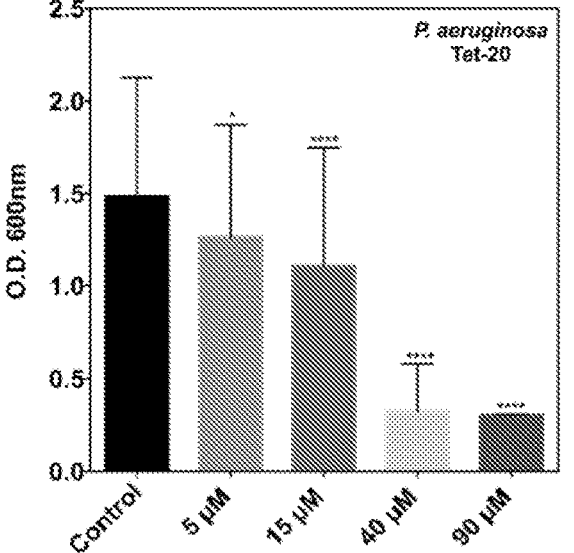
FIG. 14 illustrates determination of the Minimal Inhibition Concentration (MIC) in Tet-20 AMP. This study is after 24 hours of bacterial growth. Control (bacteria and nutrient broth and the concentration of these bacteria is $1.0 \times 10^8$ CFU/mL). These results indicate statistical differences *, , *, or **** indicated statistically differences with $p < 0.05$, $0.005 < p < 0.05$, $0.001 < p < 0.05$, and $p < 0.001$, respectively ($n = 3$ in each time point).
Figure 14:
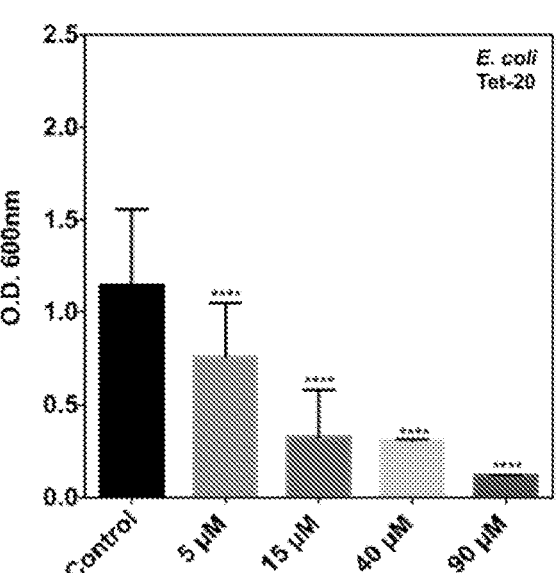
Figure 15:
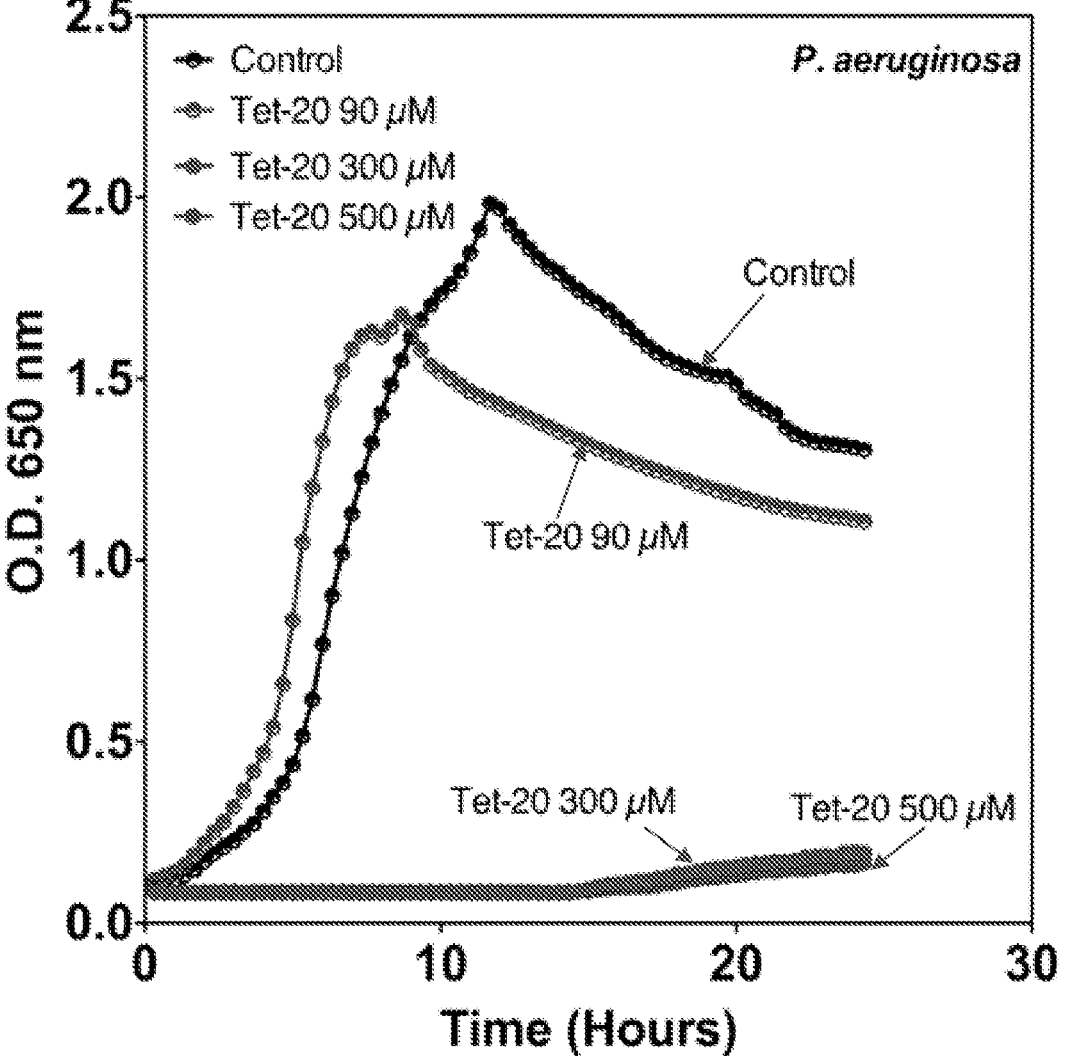
FIG. 15 illustrates the bioactivity (characterized by Minimum Biofilm Eradication Concentration, or MBEC) of Tet-20 loaded at different concentrations (90 μM, 180 μM and 300 μM) in *P. aeruginosa* (ATCC 27853). The initial concentration is $1.0 \times 10^8$ CFU/mL. The control sample is bacteria and nutrient broth without peptide. Viability of the bacteria after penetrating the bacterial biofilm for 24 h in nutrient broth at 37° C.
Figure 16:
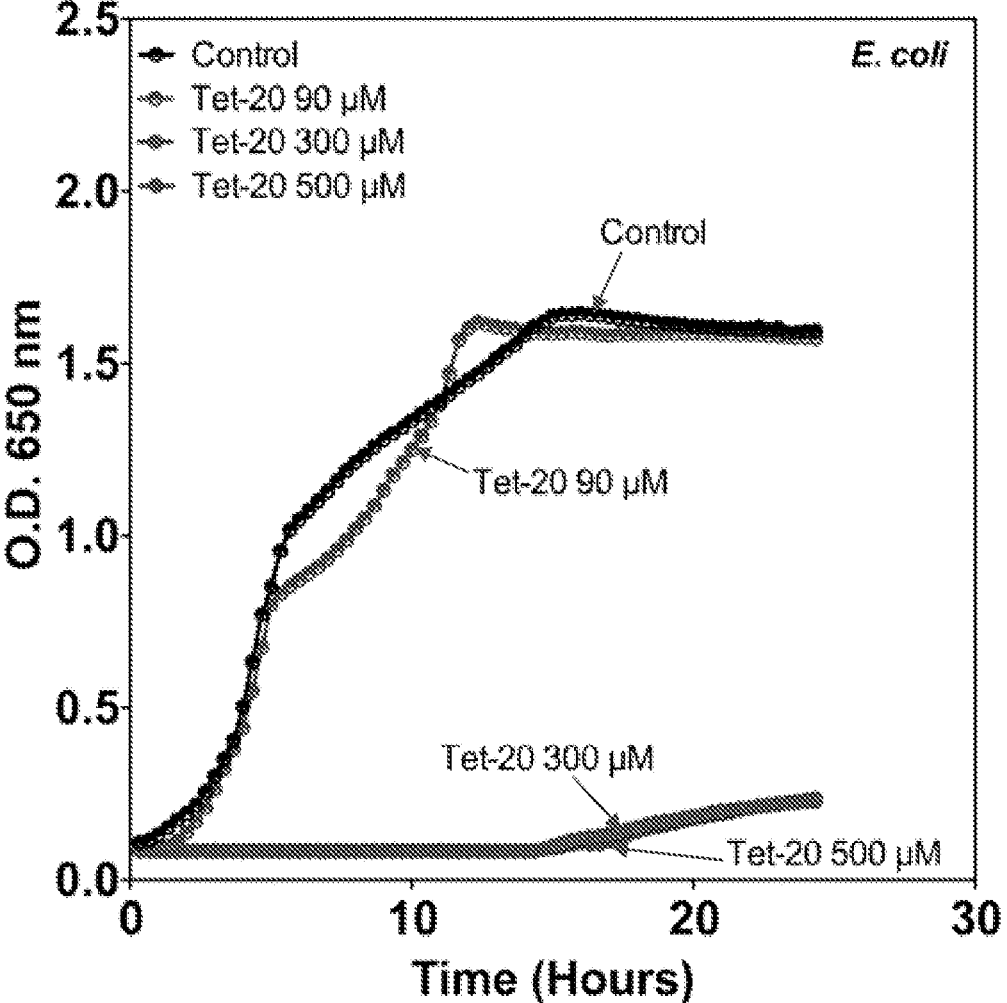
FIG. 16 illustrates the bioactivity (characterized by Minimum Biofilm Eradication Concentration, or MBEC) of Tet-20 loaded at different concentrations (90 μM and 300 μM) in *E. coli* (ATCC 25922). The initial concentration is $1.0 \times 10^8$ CFU/mL. The control sample is bacteria and nutrient broth without peptide. Viability of the bacteria after penetrating the bacterial biofilm for 24 h in nutrient broth at 37° C.

For the purposes of comparison, Tet-20 was utilized as a control peptide and MIC are 40 and 15 μM in P. aeruginosa and E. coli, respectively (FIG. 14). Tet-20 antimicrobial peptide is a traditional control with antifouling activity. The primary structure of this peptide is KRWRIRVRVIRKC (SEQ ID NO: 4) and has a broad antimicrobial activity. In addition, the value of the MBEC assay is 300 μM in both bacteria. In FIGS. 15-16, a bactericidal effect in both bacteria was observed. This effect is attributed to the hydrophilic and cationic properties of the Tet-20 peptide.

Example 3—Peptide Coupling to PEG Polymers

Bioconjugation Reaction

Once the modified MH5C peptide with a C-terminal cysteine was thoroughly characterized, we proceeded to perform the bioconjugation reaction between the PEG and modified MH5C-Cys according to Scheme1 depicted in FIG. 1. In this reaction, the reduced cysteine was allowed to react with the maleimide modified PEG's in the range of 2 and 5 kDa in weight. In this reaction, the thiol group performs a nucleophilic attack to the carbon of the double bond located in the maleimide linked to PEG. This occurs due to maleimide specific reactivity towards thiols as stated in previous articles.[18, 47-48]

In the bioconjugation, the PEG polymers were used with the following specifications: mPEG-Maleimide monofunctional 2 kDa (cat. number PSB-235), mPEG-Maleimide 5 kDa (cat. number PLS-234) obtained from Creative PEG Works Co. Nanopure water (np) (18.2 MW·cm2, MilliQ Direct 16) was used at all times.

First, the samples of modified antimicrobial peptide (MH5C-Cys) and PEG polymer (2 kDa and 5 kDa) were dissolved in DPBS 1X, pH 7 (4 mg/mL and 60 mg/mL). Prior to the reaction, oxygen was removed from each PEG polymer solution using nitrogen gas. MH5C-Cys peptides were linked through disulfide bonds formed by the addition of a cysteine group in the amino terminal of the peptide. To break these disulfide bonds, TCEP 10 mM at pH 7.0 was added in the peptide sample at a ratio of 1:1 (MH5C-Cys: TCEP 10 mM; thus, the TCEP final concentration was 5 mM).[33-34] Then, the modified PEG was added to the MH5C-Cys mixture and allowed to react for 12 hours at 4° C. in absence of oxygen to produce MH5C-Cys conjugated with PEG.

Size Exclusion

After the reaction, the conjugates were purified via size exclusion in order to remove any unreacted molecules from the bioconjugation process.[49] The isocratic method was performed for the MH5C-Cys conjugated using an FPLC system AKTA Explorer 100 (GE Healthcare). The sample of conjugated peptide was loaded onto the column Superdex peptide 10/300 GL at 0.25 mL/min monitoring at 220 nm of absorbance. DPBS 1×, pH 7 solvent was used in this experiment. The elution fractions were collected using automatic fraction collector.

Figure 9:
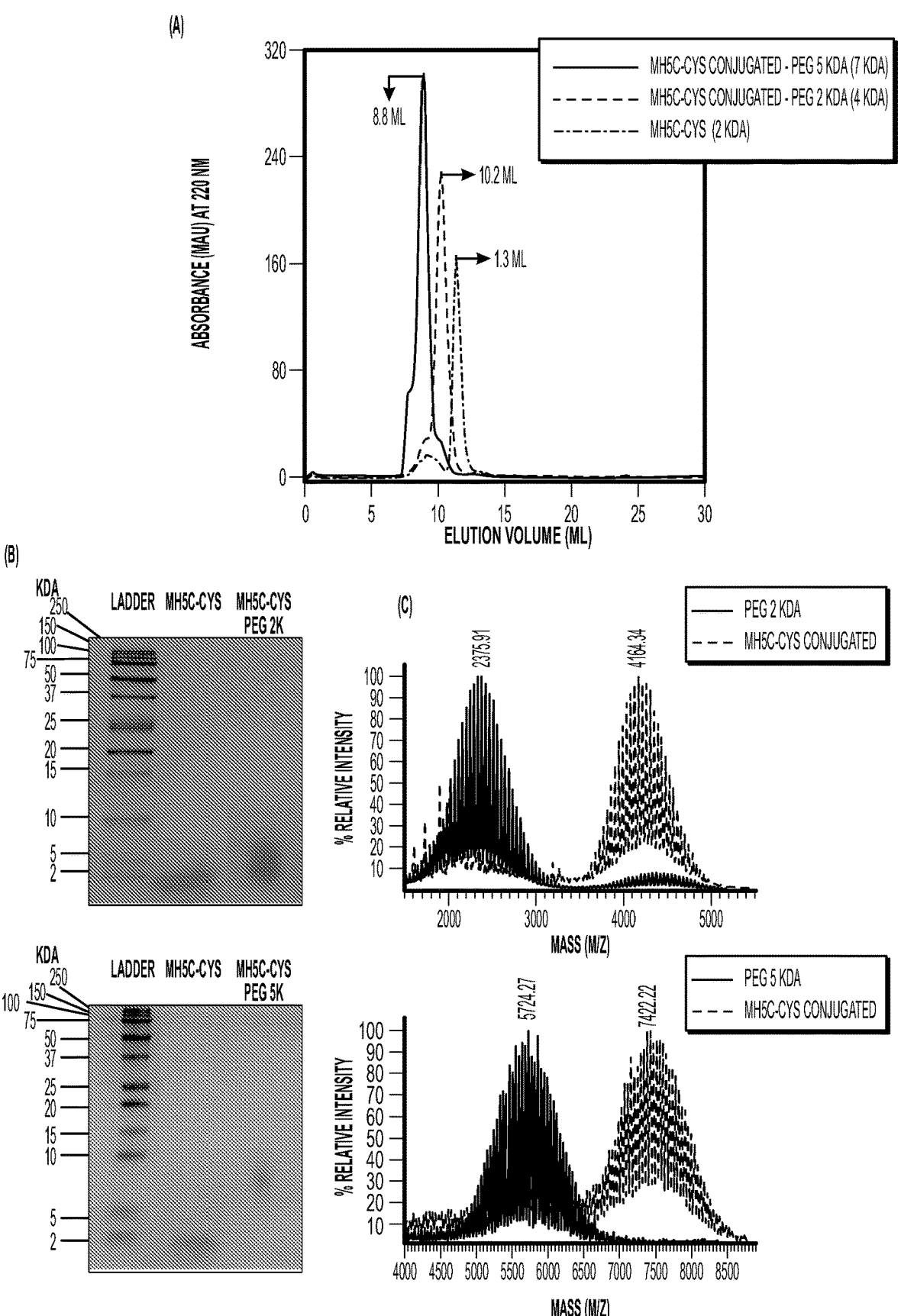
FIGS. 9(A)-9(C) illustrate the characterization of the peptide-polymer conjugates.

Thereafter, the fractions of interest were collected and analyzed by SDS-PAGE and MALDI ToF (see FIG. 9). SDS-PAGE and MALDI results show clear bands and molecular weights corresponding to the synthesized AMP-PEG conjugates. The analytical size exclusion results present three peaks corresponding to the elution fraction profile of the conjugates. The first peak in the chromatogram is the MH5C-Cys conjugated with PEG 2 kDa, the second peak is a MH5C-Cys conjugated with PEG 5 kDa and finally the third peak is the unreacted MH5C-Cys with the lowest molecular weight (FIG. 9A).

SDS-PAGE

This method was used to validate the conjugation of MH5C-Cys peptide and PEG polymer through differences in molecular weights. In this analysis, 1 mg/mL (MH5-C) and 1.5 mg/mL (MH5-C conjugates) were then loaded into a precast 16.5% Criterion™ Tris-Tricine Gel with Precision Plus Protein™ Dual Xtra Prestained Protein Standard ladder. Subsequently, electrophoresis was performed at room temperature for 1:20 hour at 125V with running buffer solution (1× Tris/Tricine/SDS Running Buffer). Once the SDS-PAGE run was completed, gels were rinsed in a fixing solution (40% methanol, 10% acetic and 50% np water) for 30 minutes. Gels were then stained using Bio-Safe™ Coomassie G-250 Stain for 1 hour. Finally, gels were washed three times for 30 minutes each time.

In SDS-PAGE, for the conjugate with PEG 2 kDa, two main bands running at 2 kDa and 4 kDa in size were observed. Similarly, with the PEG 5 kDa conjugate, two main bands at 2 kDa and 7 kDa were observed, the first bands corresponding to the MH5C-Cys and the latter the MH5C-Cys conjugated with PEG (FIG. 9B).

MALDI ToF

Mass spectrometry analysis was used to determine the specific molecular weight of the PEG-peptide conjugates. For purification and concentration of PEG-peptide conjugates a reversed phase chromatography (Pierce C18 Spin Columns, catalog number: 89870) was used. After purification, samples containing 2 mg/mL of peptide (MI-15-C), 2 mg/mL of peptide-polymer conjugates and 30 mg/mL of PEG polymer were mixed (1:6, sample/matrix solution) with the MALDI matrix solution (sinapinic acid in 70% Acetonitrile and 0.07% of Trifluoroacetic acid). Samples were then spotted on to a MALDI target plate and allowed to dry at room temperature. MALDI MS data were acquired in positive ion linear mode on a4800 Plus MALDI TOF/TOF Analyzer (Sciex) that was calibrated externally using the Opti ToF TIS Calibration Insert (Sciex). (027943, Sciex).

Figure 17:
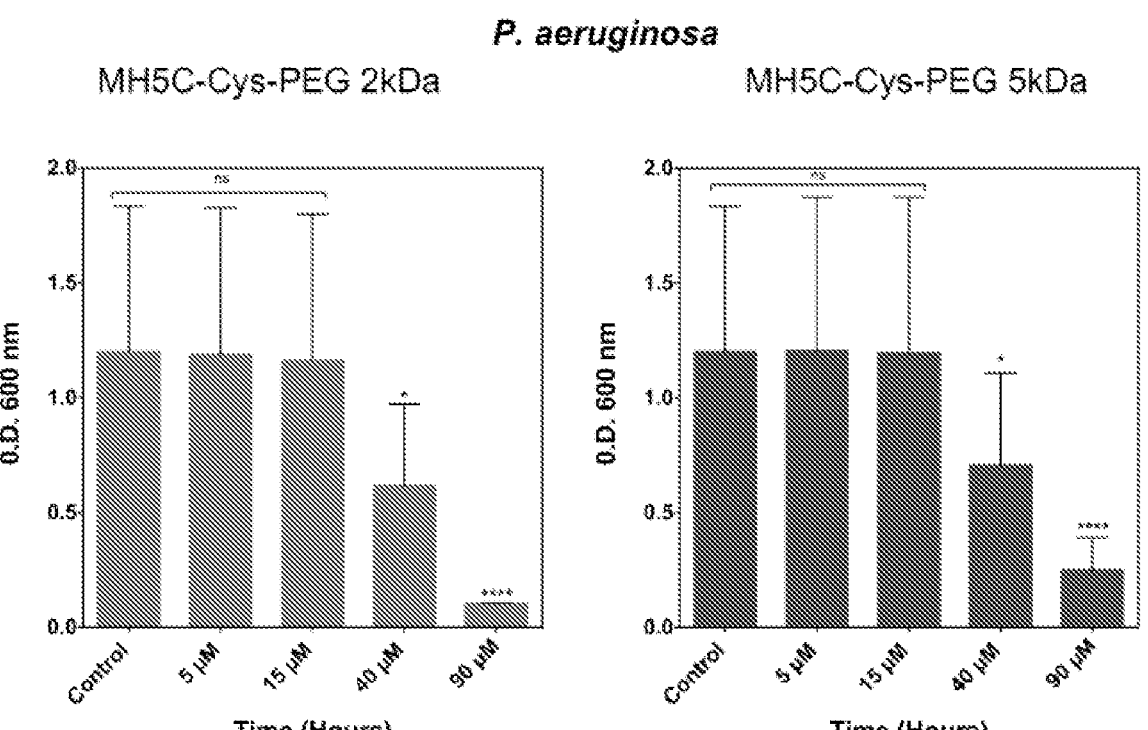
FIG. 17 illustrates the bioactivity (characterized by Minimum Inhibitory Concentration, or MIC) of MH5C-Cys conjugated loaded at different concentrations (5 μM, 15 μM, 40 μM and 90 μM) in *P. aeruginosa* (ATCC 27853). MH5C-Cys-PEG 2 kDa (light gray bars) and MH5C-Cys-PEG 5 kDa (dark gray bars). The initial concentration is $1.0 \times 10^8$ CFU/mL. The control sample is bacteria and nutrient broth without peptide. These results indicate statistical differences *, , *, or **** indicated statistically differences with $p < 0.05$, $0.005 < p < 0.05$, $0.001 < p < 0.05$, and $p < 0.001$, respectively ($n = 3$ in each time point).
Figure 18:
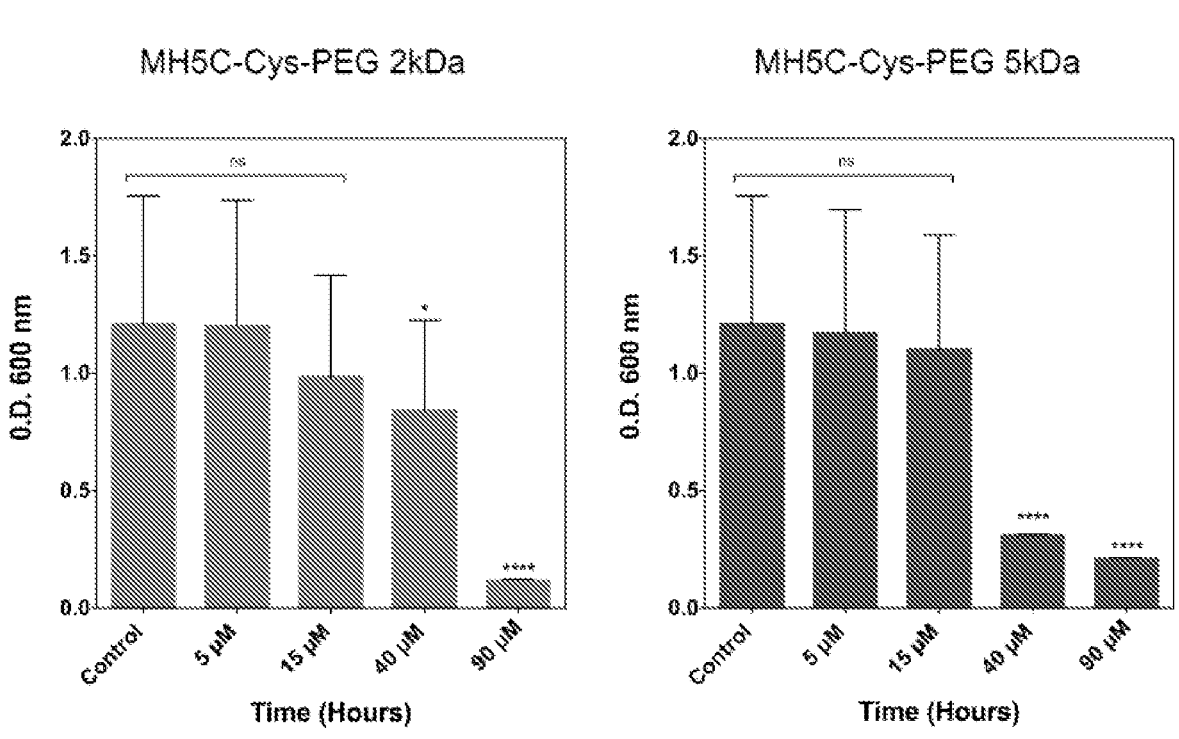
FIG. 18 illustrates the bioactivity (characterized by Minimum Inhibitory Concentration, or MIC) of MH5C-Cys conjugated loaded at different concentrations (5 μM, 15 μM, 40 μM and 90 μM) in *E. coli*. (ATCC 25922). MH5C-Cys-PEG 2 kDa (light gray bars) and MH5C-Cys-PEG 5 kDa (dark gray bars). The initial concentration is $1.0 \times 10^8$ CFU/mL. The control sample is bacteria and nutrient broth without peptide. These results indicate statistical differences *, , *, or **** indicated statistically differences with $p < 0.05$, $0.005 < p < 0.05$, $0.001 < p < 0.05$, and $p < 0.001$, respectively ($n = 3$ in each time point).

Since the peptide utilized in these experiments (i.e. MH5C-Cys) has a molecular weight of 2,126 Da and the PEG used has a molecular weight of 2 and 5 kDa, an increased in the molecular weight is expected for the peptides-conjugates (e.g., 2,126 (MH5C-Cys)+2000 Da=4126 Da). Indeed, results in FIG. 9C shows a displacement to the right for the peptides-conjugates, which correspond to an increase in the molecular weights.[50] After the synthesis of the polymer-peptide conjugates, MIC values were determined at 40 μM for both conjugates (FIGS. 17-18).

Specifically, for the conjugate with PEG 2 kDa two peaks at 2375 m/Z (PEG 2 kDa) and 4164 m/Z (MH5C-Cys conjugated with PEG) were observed and similarly for the 5 kDa, two peaks at 5724 m/Z (PEG 5 kDa) and 7422 m/Z (MH5C-Cys conjugated with PEG) were observed. Altogether, these results clearly provide proof that the synthesized conjugates were successfully obtained.

Example 4—Antimicrobial Activity of Peptide-Polymer Conjugates

In order to answer the question as to whether the PEG conjugates of MH5C-Cys retain preventive antimicrobial efficacy, we performed growth inhibition tests and SEM images with both *P. aeruginosa* and *E. coli*.

Figure 10:
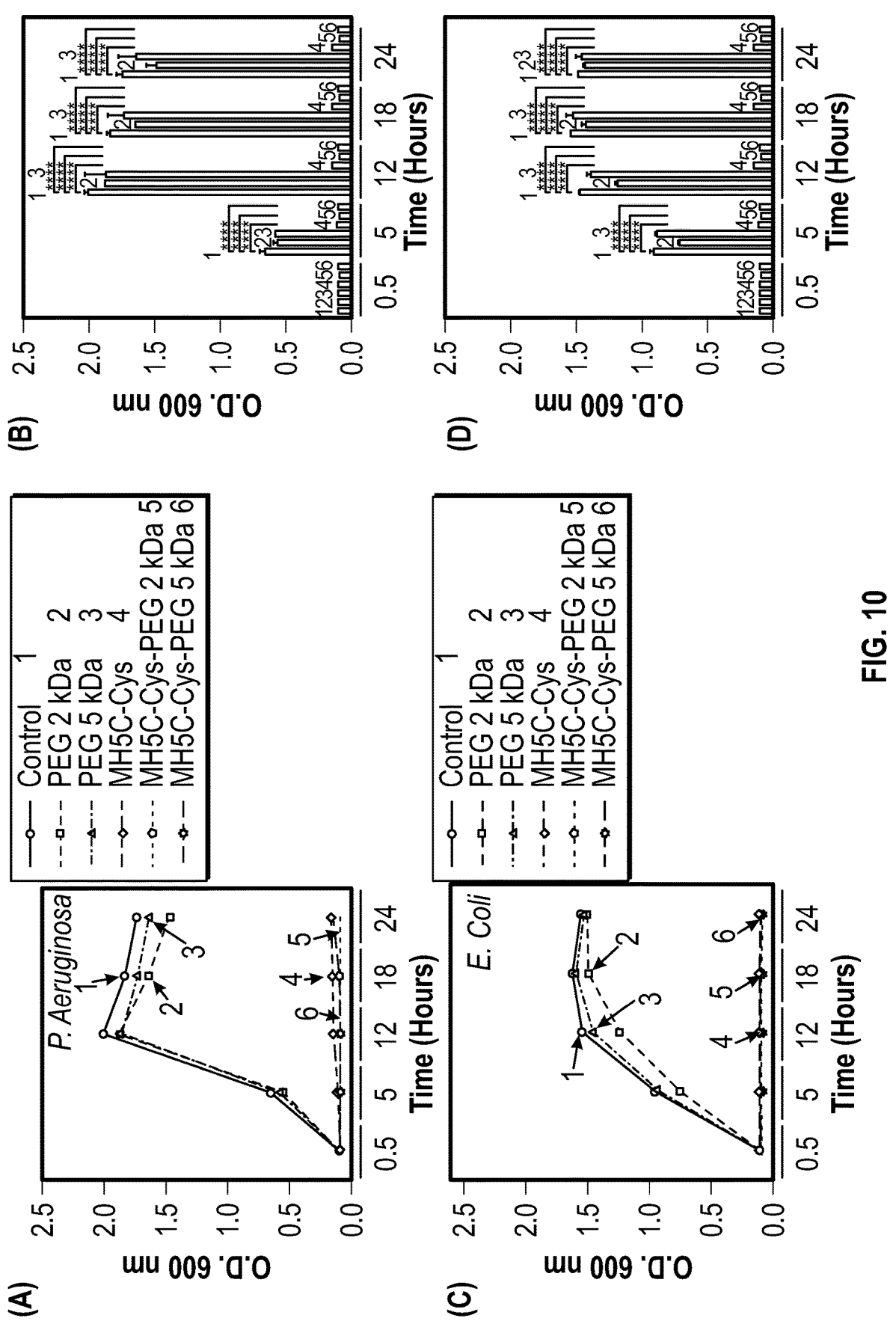
FIGS. 10(A)-10(J) illustrate bacterial growth inhibition tests and SEM using MH5C-Cys conjugated.

As can be seen in FIG. 10 all the synthesized conjugates present antimicrobial activity. In FIG. 10A and FIG. 10C the growth curves for both bacteria, *P. aeruginosa* and *E. coli* are presented, respectively. Both of the conjugates studied presented bactericidal effect and did not allow bacterial growth. Additionally, the PEG polymer alone did not present any significant effect in preventing the growth of the bacteria, which evidences that the conjugated peptide remains active after conjugation. FIG. 10B and FIG. 10D show the statistically significant differences between control and MH5C-Cys PEG conjugates (P<0.0001; n=3 in each time point). Moreover, SEM images were recorded to account for the biofilm formation, and a significant prevention of the bacteria biofilm was observed. This allows the conclusion that the conjugates do not allow the quorum sensing of bacteria in the biofilm process; see FIG. 10F and FIG. 10G (*P. aeruginosa*), FIG. 10I and FIG. 10J (*E. coli*).[51] This is an important finding as it proves that the peptide's function is retained after the covalent attachment into a conjugate. See e.g., Singh et al., *Biomacromolecules*. 14; 15(4):1337-45 (2014).

Figure 11:
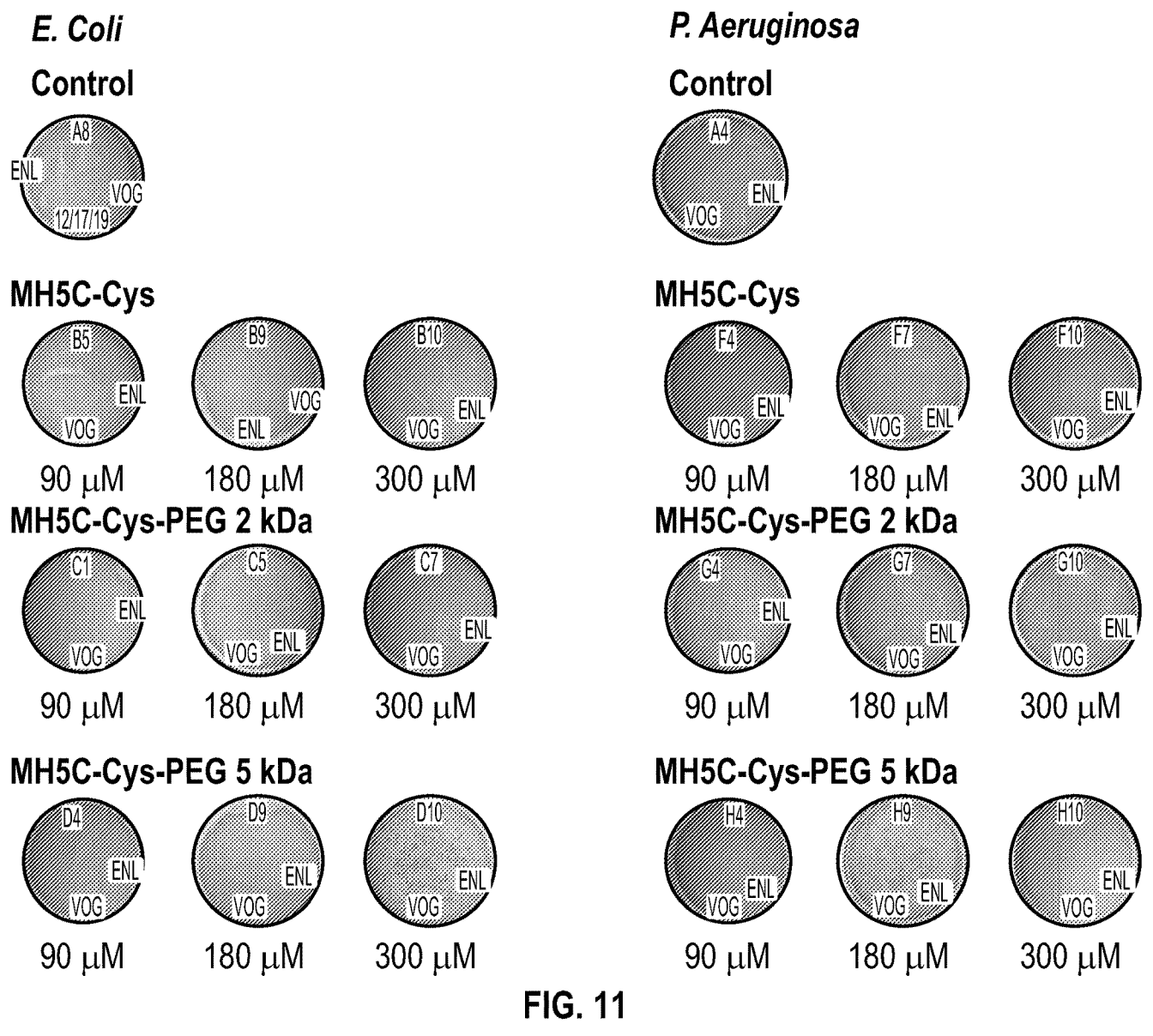
Figure 12:
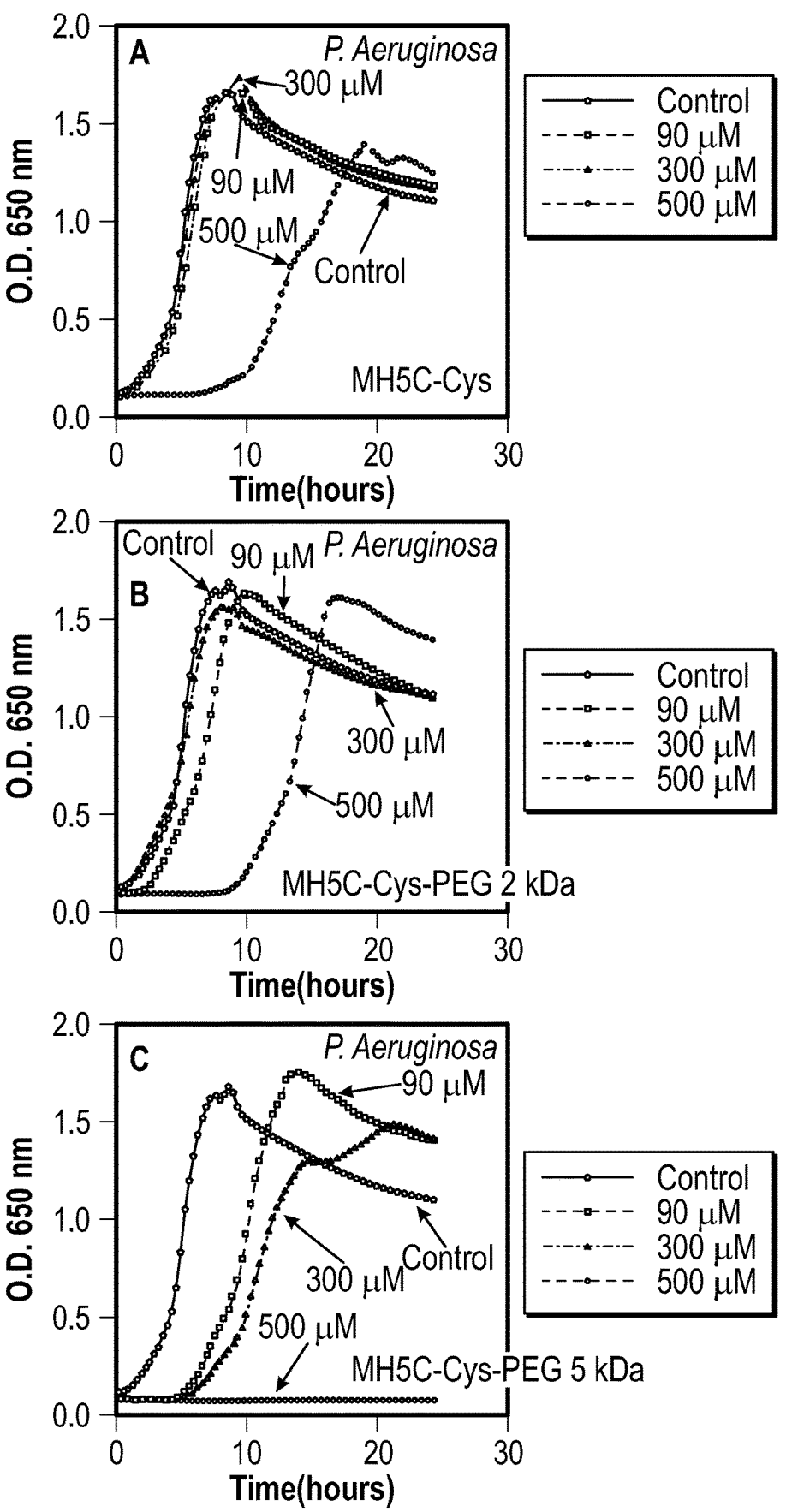
FIGS. 12(A)-12(C) illustrate Minimum Biofilm Eradication Concentration (MBEC) results after 24 hours with *P.*
Figure 13:
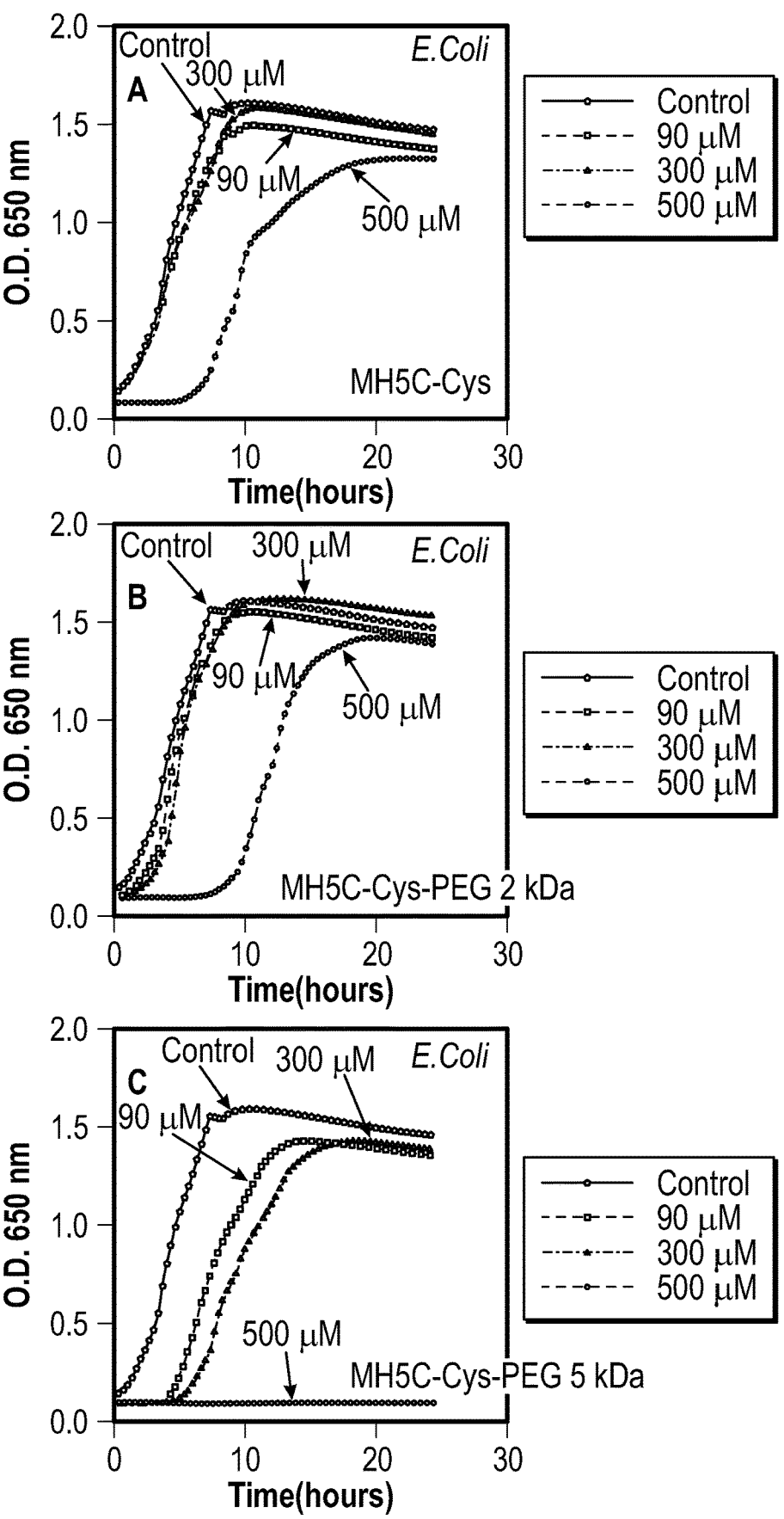
FIGS. 13(A)-13(C) illustrate MBEC results after 24 hours with *E. coli*.

To extend the understanding of the conjugates efficacy to prevent or eradicate the biofilm, the MBIC and MBEC assays were performed (FIGS. 11-13).

Determination of Minimum Biofilm Inhibition using MBIC Assay

MBIC (Minimum Biofilm Inhibitory Concentration) was determined by the adherence assay using the Calgary Biofilm Device (Innovotech Inc.). In this assay, the bacteria and compounds (MH5C-Cys and both PEG conjugates) were placed together in the assay plate for 72 h to allow growth. Afterwards, CFU (Colony Forming Unit) and optical density measurements for each well were recorded at 650 nm and clear wells and growth inhibition curves were taken as evidence of biofilm inhibition.

In MBIC, a value of 300 μM in *P. aeruginosa* and 300 μM in *E. coli* for MH5C-Cys-PEG 5 kDa was determined. According to the results in FIG. 11, the MH5C-Cys without polymer and MH5C-Cys-PEG 2 kDa does not possess a significant inhibition against the biofilm formation process. However, MH5C-Cys-PEG 5 kDa did present the inhibition of the biofilm for *P. aeruginosa* and *E. coli*.

Determination of Minimum Biofilm Eradication using MBEC Assay

In order to assess the biofilm eradication activity (MBEC) of these compounds, biofilms of the *P. aeruginosa* and *E. coli* were grown in a Calgary Biofilm Device (Innovotech Inc.) The device consists of various parts: a plate containing the inoculated test medium and a polyethylene glycol lid with 96 identical wells on which the microbial biofilm forms under incubating with shaking. The assay was conducted according to the MBEC protocol as supplied by the manufacturer. Inoculum of each bacterium was prepared in TSB (Tryptic Soy Broth) to a final density of $1.0 \times 10^6$. In each well of the 96 well plate, 150 of the inoculated media was transferred. Assay plates were placed in an incubator for 72 h to allow growth and comparison of biofilms was performed for each bacteria strain. After 72 h, the PEG lid of the MBEC assay was transferred to a 'challenge' plate. Essentially, serial dilutions of each conjugated (4 kDa and 7 kDa), antimicrobial peptide, and PEG polymers were prepared in TSB to a final volume in the well plates of 200 μL (control and conjugates at 90 μM, 300 μM, and 500 μM). After exposure of the biofilm to the antimicrobial challenge for 24 h, the PEG lid was removed from the challenge plate, and the optical density measurements for each plate were recorded at 650 nm. Clear wells were taken as evidence of biofilm eradication, and MBEC values were assigned as the lowest concentration at which no growth was observed after 24 h of incubation.[31-32]

The results show that the MH5C-Cys and PEG conjugates are able to eradicate the biofilm at a concentration of 500 μM. For each bacterium this effect is observed during the first growth phase. Indeed, the bacteria is not able to start the logarithmic growth phase until after 10 hours when compared to the MH5C-Cys.

Figure 19:
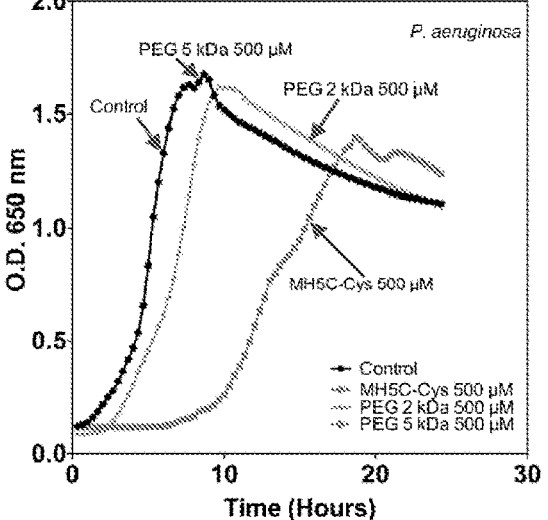
FIG. 19 illustrates the bioactivity (characterized by Minimum Biofilm Eradication Concentration, or MBEC) results after 24 hours in *P. aeruginosa* and *E. coli*. The initial concentration of bacteria is $1.0 \times 10^8$ CFU/mL. The samples are control (nutrient broth and bacteria), PEG 2 kDa, PEG 5 kDa (nutrient broth, bacteria and PEG polymer) and MH5C-Cys loaded at 500 μM.
Figure 19:
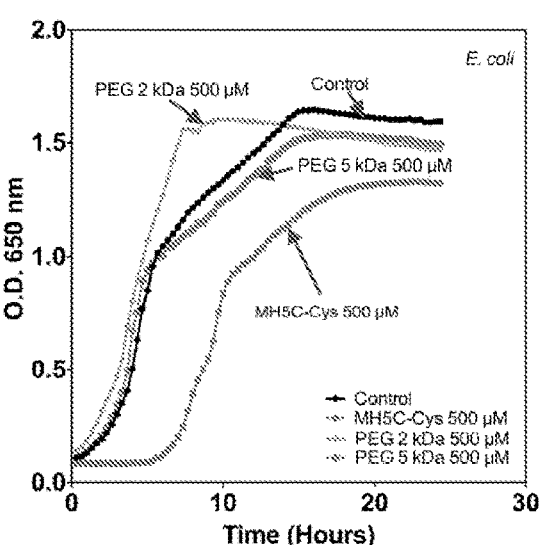

In FIGS. 12A-12C and 13A-13C, MH5C-Cys and conjugates have an effect for approximately 8-10 h, where they did not allow bacterial growth. After this time, slow bacterial growth is observed compared to control samples (control, nutrient broth and bacteria; PEG 2 kDa, PEG 5 kDa, nutrient broth, bacteria and PEG polymer), see also FIG. 19. Interestingly, for the MH5C-Cys-PEG 5 kDa conjugate this effect is more noticeable. These findings lead to the conclusion that the chemical and physical interactions of the conjugate with the bacterium are enhanced when a larger polymeric hydrophilic tail is utilized. The results show that PEG 5 kDa protects the conjugate from proteases in the biofilm formation.

In summary (FIG. 20), MICs and MBICs demonstrate that both tested strains of Gram-negative bacteria remain in the planktonic phase after direct contact with the proposed conjugated compounds. In general, the peptide MH5C-Cys conjugated to a PEG polymer of 5 kDa exhibited significant prevention and inhibition of biofilm formation for *P. aeruginosa* and *E. coli*. In the same way, this conjugate presented biofilm eradication activity. According to the MICs (90 μM) and MBICs (300 *P. aeruginosa* and 300 μM in *E. coli*) it can be concluded that this conjugate has an intense action that prevents the formation of biofilms; and is capable of eradicating biofilms (MBEC 500 μM). In contrast, the MH5C-Cys peptide with PEG polymer 2 kDa did not show significant eradication (FIGS. 12-13) nor prevention/inhibition (FIG. 11) of the biofilm in comparison to the 5 kDa conjugate.

These results demonstrate that the peptide conjugates of the present technology are useful in methods for treating or preventing formation of biofilms and biofouling.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

Each and every publication and patent mentioned in the above specification is herein incorporated by reference in its entirety for all purposes. Various modifications and variations of the described methods and system of the present technology will be apparent to those skilled in the art without departing from the scope and spirit of the present technology. Although the present technology has been described in connection with specific embodiments, the present technology as claimed should not be unduly limited to such specific embodiments. Indeed, various modifications of the described modes for carrying out the present technology which are obvious to those skilled in the art and in fields related thereto are intended to be within the scope of the following claims.

REFERENCES (1) Russo, T. A., Johnson, J. R. Medical and economic impact of extra-intestinal infections due to *Escherichia coli*: focus on an increasingly important endemic problem. Microbes and infection 2003, 5(5), 449-456.

(2) Loveday, H. P., Wilson, J.; A., K., K., Pitchers, R., Walker, J. T., Browne, J. Association between healthcare water systems and *Pseudomonas aeruginosa* infections: a rapid systematic review. Journal of Hospital Infection 2014, 86(1), 7-15.

(3) Driscoll, J. A., Brody, S. L., Kollef, M. H. The epidemiology, pathogenesis and treatment of *Pseudomonas aeruginosa* infections. Drugs 2007, 67(3), 351-368.

(4) Luca, V., Stringaro, A., Colone, M., Pini, A., Mangoni, L., M. Esculentin (1-21), an amphibian skin membrane-active peptide with potent activity on both planktonic and biofilm cells of the bacterial pathogen *Pseudomonas aeruginosa*. Cellular and Molecular Lifesciences 2013, 70(15), 2773-2786.

(5) Roux, A., Beloin, C., Ghigo, J. M. Combined inactivation and expression strategy to study gene function under physiological conditions: application to identification of new *Escherichia coli* adhesins. J. Bacteriol. 2005, 187(3), 1001-1013.

(6) Brady, E., A. S., Kang, S.; Elimelech, M. A single-walled-carbon-nanotube filter for removal of viral and bacterial pathogens. Small 2008, 4(4), 481-484.

(7) Pendergast, M. M. H., E. M.; V. A review of water treatment membrane technologies. Energy and Environmental Science 2014, 4, 1946-1971.

(8) Savage, N. D., M. S. Nanomaterials and water purification: Opportunities and challenges. J. Nanopart. Res. 2005, 331-342.

(9) Ergene, C., Yasuhara, K., Palermo, E. F. Biomimetic antimicrobial polymers: recent advances in molecular design. Polymer Chemistry 2018, 9(18), 2407-2427.

(10) Qian, Y.; Qi, F.; Chen, Q.; Zhang, Q.; Qiao, Z.; Zhang, S.; Wei, T.; Yu, Q.; Yu, S.; Mao, Z.; Gao, C.; Ding, Y.; Cheng, Y.; Jin, C.; Xie, H.; Liu, R. Surface Modified with a Host Defense Peptide-Mimicking β-Peptide Polymer Kills Bacteria on Contact with High Efficacy. ACS Applied Materials & Interfaces 2018, 10 (18), 15395-15400, DOI: 10.1021/acsami.8b01117.

(11) Kumar, P. K., J.; Straus, S., Antimicrobial peptides: Diversity, mechanism of action and strategies to improve the activity and biocompatibility in vivo. Biomolecules 2018, 8(1), 4.

(12) Fox, J. L. Antimicrobial peptides stage a comeback. Nat. Biotechnol. 2013.

(13) Roncevic, T., Vukicevic, D., Krce, L., Benincasa, M., Aviani, I., Maravic, A., Tossi, A., Selection and redesign for high selectivity of membrane-active antimicrobial peptides from a dedicated sequence/function database. Biochimica et Biophysica Acta (BBA)—Biomembranes 2019, 1861(4), 827-834.

(14) Pushpanathan, M.; Gunasekaran, P.; Rajendhran, J. Antimicrobial peptides: versatile biological properties. International Journal of Peptides 2013.

(15) Lai, R.; Zheng, Y.-T.; Shen, J.-H.; Liu, G.-J.; Liu, H.; Lee, W.-H.; Tang, S.-Z.; Zhang, Y. Antimicrobial peptides from skin secretions of Chinese red belly toad *Bombina maxima*. Peptides 2002, 23 (3), 427-435.

(16) Lai, R. L., H.; Lee, W.; H.; Zhang, Y. An anionic antimicrobial peptide from toad *Bombina maxima*. Biochemical and Biophysical Research Communications 2002, 295, 796-799.

(17) Dennison, S. R.; Mura, M.; Harris, F.; Morton, L. H.; Zvelindovsky, A.; Phoenix, D. A. The role of C-terminal amidation in the membrane interactions of the anionic antimicrobial peptide, maximin H5. Biochimica et Biophysica Acta (BBA)-Biomembranes 2015, 1848 (5), 1111-1118.

(18) Hamley, I. W. PEG—peptide conjugates. Biomacromolecules 2014, 15(5), 1543-1559.

(19) Du, J., Bandara, H. M. H. N., Du, P., Huang, H., Hoang, K., Nguyen, D., Smyth, H. D. Improved biofilm antimicrobial activity of polyethylene glycol conjugated tobramycin compared to tobramycin in *Pseudomonas aeruginosa* biofilms. Molecular Pharmaceutics 2015, 12(5), 1544-1553.

(20) Kumar, P.; Takayesu, A.; Abbasi, U.; Kalathottukaren, M. T.; Abbina, S.; Kizhakkedathu, J. N.; Straus, S. K. Antimicrobial Peptide-Polymer Conjugates with High Activity: Influence of Polymer Molecular Weight and Peptide Sequence on Antimicrobial Activity, Proteolysis, and Biocompatibility. ACS Applied Materials & Interfaces 2017, 9 (43), 37575-37586, DOI: 10.1021/acsami.7b09471.

(21) Darling, S. B. Perspective: Interfacial materials at the interface of energy and water. J. Appl. Phys. 2018, 124 (3), 030901.

(22) Mena, K. D., Gerba, C. P. Risk assessment of *Pseudomonas aeruginosa* in water. Reviews of Environmental Contamination and Toxicology 2009, 201, 71-115.

(23) Edberg, S. C. L., Rice, E. W., Karlin, R. J., Allen, M. J. *Escherichia coli*: the best biological drinking water indicator for public health protection. Journal of Applied Microbiology 2000, 88.

(24) Lorber, B., Fischer, F., Bailly, M., Roy, H., Kern, D. Protein analysis by dynamic light scattering: methods and techniques for students Biochemistry and Molecular Biology Education 2012, 40 (6), 372-382.

(25) Nobbmann, U. PDI from an individual peak in DLS. 2015.

(26) Dennison, S. R., Mura, M., Harris, F., Morton, L. H., Zvelindovsky, A., Phoenix, D. A. The role of C-terminal amidation in the membrane interactions of the anionic antimicrobial peptide, maximin H5. Biochimica et Biophysica Acta (BBA) Biomembranes 2015, 1848(5), 1111-1118.

(27) Greenfield, N. J. Using circular dichroism collected as a function of temperature to determine the thermodynamics of protein unfolding and binding interactions. Nature protocols 2006, 1 (6), 2527-2535.

(28) Jorgensen, J. H. T., J. D. Susceptibility test methods: dilution and disk diffusion methods. Manual of Clinical Microbiology, Eleventh Edition American Society of Microbiology 2015, 1126-1127.

(29) Bello, S. A. J. M., I. D.; Rosim Fachini, E.; Sundaram, P. A.; Diffoot Carlo, N. In vitro evaluation of human osteoblast adhesion to a thermally oxidized γ-TiAl intermetallic alloy of composition Ti-48A1-2Cr-2Nb (at. %). Journal of Materials Science: Materials in Medicine 2010, 21(5), 1739-1750.

(30) Santillan, J., Dwomoh, E. A., Rodriguez Aviles, Y. G., Bello, S. A., Nicolau, E. Fabrication and Evaluation of Polycaprolactone Beads-on-string Membranes for Applications in Bone Tissue Regeneration. ACS Applied Bio Materials 2019.

(31) Carson, L., Chau, P. K., Earle, M. J., Gilea, M. A., Gilmore, B. F., Gorman, S. P., Seddon, K. R. Antibiofilm activities of 1-alkyl-3-methylimidazolium chloride ionic liquids. Green Chemistry 2009, 11 (4), 492-497.

(32) Lemire, J., Demeter, M., Turner, R. J. Protocols for Harvesting a Microbial Community Directly as a Biofilm for the Remediation of Oil Sands Process Water. In Hydrocarbon and Lipid Microbiology Protocols 2015, 131-152.

(33) Burns, J. A., Butler, J. C., Moran, J., Whitesides, G. M. Selective reduction of disulfides by tris (2-carboxyethyl) phosphine. The Journal of Organic Chemistry 1991, 56(8), 2648-2650.

(34) Van Leeuwen, L. A., Hinchy, E. C., Murphy, M. P., Robb, E. L., Cocheme, H. M. Click-PEGylation—a mobility shift approach to assess the redox state of cysteines in candidate proteins. Free Radical Biol. Med. 2017, 108, 374-382.

(35) Bhattacharjee, S. DLS and zeta potential—What they are and what they are not? J. Controlled Release 2016, 235, 337-351.

(36) Gerzhova, A., Mondor, M., Benali, M., Aider, M. Study of total dry matter and protein extraction from canola meal as affected by the pH, salt addition and use of zeta-potential/turbidimetry analysis to optimize the extraction conditions. Food Chem. 2016, 201, 243-252.

(37) Zeta Potential An introduction in 30 minutes. Zetasizer Nano Series technical note (MRK654-01) 2006, 1-6.

(38) Mai, X. T., Huang, J., Tan, J., Huang, Y., Chen, Y. Effects and mechanisms of the secondary structure on the antimicrobial activity and specificity of antimicrobial peptides. J. Pept. Sci. 2015, 21(7), 561-568.

(39) Gopal, R., Park, J. S., Seo, C. H., Park, Y. Applications of circular dichroism for structural analysis of gelatin and antimicrobial peptides. International Journal of Molecular Science 2012, 13(3), 3229-3244.

(40) Louis, J., C., Andrade, Navarro, M. A., Perez, Iratxeta, C. Prediction of protein secondary structure from circular dichroism using theoretically derived spectra. Proteins: Structure, Function and Bioinformatics 2012, 80(2), 374-381.

(41) Louis-Jeune, C., Andrade-Navarro, M. A., Perez-Iratxeta. Prediction of protein secondary structure from circular dichroism using theoretically derived spectra. Proteins: Structure, Function, and Bioinformatics 2012, 80(2), 374-381.

(42) Myers, J. K.; Pace, C. N.; Scholtz, J. M. Helix propensities are identical in proteins and peptides. Biochemistry 1997, 36 (36), 10923-10929.

(43) Dennison, S. R., Morton, L. H., Harris, F., & Phoenix, D. A. Low pH Enhances the Action of Maximin H5 against *Staphylococcus aureus* and Helps Mediate Lysylated Phosphatidylglycerol-Induced Resistance. Biochemistry 2016, 55(27), 3735-3751.

(44) Cavaleri, J., Rankin, D., Harbeck, J., Sautter, L. R., McCarter, S. Y., Sharp, S. E., Spiegel, A. C. Manual of antimicrobial susceptibility testing. American Society for Microbiology 2005, 12, 53-42.

(45) Mangoni, M. L.; Grovale, N.; Giorgi, A.; Mignogna, G.; Simmaco, M.; Barra, D. Structure-function relationships in bombinins H, antimicrobial peptides from *Bombina* skin secretions★. Peptides 2000, 21 (11), 1673-1679.

(46) Dennison, S. R.; Morton, L. H.; Harris, F.; Phoenix, D. A. Low pH Enhances the Action of Maximin H5 against *Staphylococcus aureus* and Helps Mediate Lysylated Phosphatidylglycerol-Induced Resistance. Biochemistry 2016, 55 (27), 3735-3751.

(47) Nair, D. P., Podgorski, M., Chatani, S., Gong, T., Xi, W., Fenoli, C. R., Bowman, C. N. The thiol-Michael addition click reaction: a powerful and widely used tool in materials chemistry. Chem. Mater. 2013, 26(1), 724-744.

(48) Lowe, A. B. Thiol-ene "click" reactions and recent applications in polymer and materials synthesis. Polymer Chemistry 2010, 1(1), 17-36.

(49) Braun, A. C., Gutmann, M., Mueller, T. D., Lühmann, T., Meinel, L. Bioresponsive release of insulin-like growth factor-I from its PEGylated conjugate. J. Controlled Release 2018, 279, 7-28.

(50) Evgrafova, Z., Voigt, B., Baumann, M., Stephani, M., Binder, W. H., Balbach, J., Probing Polymer Chain Conformation and Fibril Formation of Peptide Conjugates. Chemphyschem 2019, 20(2), 236-240.

(51) Packiavathy, I. A. S., Maruthamuthu, S., Gnanaselvan, G., Manoharan, S., Paul, J. B. J., Annapoorani, A., Ravi, A. V., The control of microbially induced corrosion by methyl eugenol—A dietary phytochemical with quorum sensing inhibitory potential. Bioelectrochemistry 2019, 128, 186-192.

What is claimed is:

1. A peptide conjugate comprising a polyethylene glycol (PEG) polymer conjugated to an antimicrobial peptide (AMP) comprising the amino acid sequence ILGPVLGLVSDTLDDVLGILC-COOH (SEQ ID NO: 2), or a PEG polymer conjugated to an AMP having an amino acid sequence of SEQ ID NO: 2, wherein the AMP is conjugated to the PEG polymer via a thiol bond, optionally wherein the PEG polymer is conjugated to the N-terminus or the C-terminus of the AMP.

2. The peptide conjugate of claim 1, wherein the AMP is between 21 to 30 amino acids in length, or between 21 to 25 amino acids in length.

3. The peptide conjugate of claim 1, wherein the PEG polymer has an average molecular weight of about 1 kDa to about 50 kDa, or 2 kDa or 5 kDa.

4. The peptide conjugate of claim 1, wherein the AMP comprises a secondary structure that is at least about 90%-95% α-helix, and/or less than about 1%, less than about 0.5%, less than about 0.1%, or less than about 0.05% β-sheet, and/or wherein the peptide conjugate further comprises a cysteine residue at the N-terminus of the AMP.

5. The peptide conjugate of claim 1, wherein the PEG polymer comprises between about 40 to about 200 ethylene oxide units or greater than about 40 ethylene oxide units or greater than about 100 ethylene oxide units.

6. An aquatic filtration membrane, wherein the filtration membrane comprises the peptide conjugate of claim 1.

7. A medical implant or device comprising a body having at least one surface, wherein the at least one surface is coated with, or includes an effective amount of the peptide conjugate of claim 1.

8. The medical implant or device of claim 7, wherein the at least one surface is coated with the peptide conjugate at a surface density ranging from 0.4 to 275 micrograms per square centimeter, and/or wherein the at least one surface is composed of a synthetic carbon polymer and/or a polypeptide.

9. The medical implant or device of claim 7, wherein the medical implant is a vascular graft, or wherein the medical device is selected from the group consisting of a fracture fixation system, a tubular device that penetrates a body tissue of a patient, and a component of an intubation system.

10. The medical implant or device of claim 9, wherein the fracture fixation system is a nail, a bolt, or a screw, or wherein the tubular structure is selected from the group consisting of an intubation tube, a feeding tube, an endotracheal tube, a catheter, and a shunt.

11. A method for fabricating a medical device or implant that is configured to eradicate or prevent biofilm formation comprising contacting at least one surface of a body of a medical device or implant with an effective amount of the peptide conjugate of claim 1.

12. A method for treating an infection caused by a microbial pathogen in a subject in need thereof comprising administering to the subject the medical implant or device of claim 7, wherein the microbial pathogen comprises a population of P. aeruginosa or E. coli.

13. The method of claim 12, wherein the subject suffers from or is at risk for endocarditis, urinary tract infections, biliary sepsis, pneumonia, gastroenteritis, cystic fibrosis, or burn wounds.

14. The method of claim 12, wherein the MIC or MBEC of the peptide conjugate is between about 50 µM and about 500 µM.

15. A method for eradicating biofilm formation caused by a microbial pathogen in a subject in need thereof comprising administering to the subject the medical implant or device of claim 7, wherein the microbial pathogen comprises a population of P. aeruginosa or E. coli.

16. A method for reducing microbial biofilm formation on a surface comprising contacting the surface with an effective amount of a composition comprising the peptide conjugate of claim 1, wherein the microbial biofilm formation is caused by P. aeruginosa or E. coli.

17. A method for inhibiting growth of a microbe population on a surface comprising contacting the surface with an effective amount of a composition comprising the peptide conjugate of claim 1, wherein the microbe population comprises P. aeruginosa or E. coli.

18. A method for reducing aquatic biofouling in an aquatic environment comprising: contacting the aquatic environment with an effective amount of the peptide conjugate of claim 1.

19. A method for preventing or reducing biofilm formation in water comprising contacting the water with an effective amount of a composition comprising the peptide conjugate of claim 1, wherein the biofilm formation is caused by P. aeruginosa or E. coli, optionally wherein the contacted water is applied to a reverse osmosis filter.

20. A method for preventing or reducing biofilm formation in a fluid medium comprising contacting the fluid medium with an effective amount of a composition comprising the peptide conjugate of claim 1, wherein the biofilm formation is caused by P. aeruginosa or E. coli, optionally wherein the fluid medium is applied to a reverse osmosis filter.

* * * * *

SEQUENCE LISTING

```
<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Leu Gly Pro Val Leu Gly Leu Val Ser Asp Thr Leu Asp Asp Val
1               5                   10                  15

Leu Gly Ile Leu
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Leu Gly Pro Val Leu Gly Leu Val Ser Asp Thr Leu Asp Asp Val
1               5                   10                  15

Leu Gly Ile Leu Cys
            20

<210> SEQ ID NO 3
<211> LENGTH: 20
<212> TYPE: PRT
<213> ORGANISM: Bombina maxima

<400> SEQUENCE: 3

Ile Leu Gly Pro Val Leu Gly Leu Val Ser Asp Thr Leu Asp Asp Val
1               5                   10                  15
```

-continued

```
Leu Gly Ile Leu
          20

<210> SEQ ID NO 4
<211> LENGTH: 13
<212> TYPE: PRT
<213> ORGANISM: Unknown
<220> FEATURE:
<223> OTHER INFORMATION: Description of Unknown:
      Tet-20 antimicrobial peptide sequence

<400> SEQUENCE: 4

Lys Arg Trp Arg Ile Arg Val Arg Val Ile Arg Lys Cys
1               5                   10
```